(12) United States Patent
Chae

(10) Patent No.: US 11,642,323 B2
(45) Date of Patent: May 9, 2023

(54) METHOD FOR MODULATING METABOLISM

(71) Applicant: Brightseed, Inc., South San Francisco, CA (US)

(72) Inventor: Lee Heil Chae, San Francisco, CA (US)

(73) Assignee: Brightseed, Inc., South San Francisco, CA (US)

( * ) Notice: Subject to any disclaimer, the term of this patent is extended or adjusted under 35 U.S.C. 154(b) by 0 days.

(21) Appl. No.: 17/813,875

(22) Filed: Jul. 20, 2022

(65) Prior Publication Data

US 2022/0370383 A1 Nov. 24, 2022

Related U.S. Application Data

(63) Continuation of application No. 17/501,230, filed on Oct. 14, 2021, which is a continuation of application No. 16/961,035, filed as application No. PCT/US2019/012993 on Jan. 10, 2019, now Pat. No. 11,173,136.

(60) Provisional application No. 62/615,671, filed on Jan. 10, 2018.

(51) Int. Cl.
*A61K 31/165* (2006.01)
*A61P 1/16* (2006.01)

(52) U.S. Cl.
CPC .............. *A61K 31/165* (2013.01); *A61P 1/16* (2018.01)

(58) Field of Classification Search
CPC .................................................. A61K 31/165
See application file for complete search history.

(56) References Cited

U.S. PATENT DOCUMENTS

| | | |
|---|---|---|
| 5,605,793 A | 2/1997 | Stemmer |
| 5,811,238 A | 9/1998 | Stemmer et al. |
| 5,830,721 A | 11/1998 | Stemmer et al. |
| 5,837,458 A | 11/1998 | Minshull et al. |
| 6,265,185 B1 | 7/2001 | Muller et al. |
| 6,316,209 B1 | 11/2001 | Baekkeskov et al. |
| 6,368,837 B1 | 4/2002 | Gatenby et al. |
| 6,391,651 B1 | 5/2002 | Maclaren et al. |
| 6,521,748 B2 | 2/2003 | Tang |

(Continued)

FOREIGN PATENT DOCUMENTS

| | | |
|---|---|---|
| CN | 107510706 | 12/2017 |
| EP | 1 671 534 | 6/2006 |

(Continued)

OTHER PUBLICATIONS

Chen et al. (Int. J. Mol. Sci. 2013, 14(6), 12581-12592). (Year: 2013).*

(Continued)

*Primary Examiner* — Benjamin J Packard
(74) *Attorney, Agent, or Firm* — Knobbe, Martens, Olson & Bear, LLP

(57) ABSTRACT

A method for modulating metabolism is provided which includes the step of providing a consumable composition including an extract containing a compound of Formula I to a subject in need thereof thereby modulating the subject's metabolism and addressing the underlying pathogenesis of metabolic disorders, such as nonalcoholic fatty liver disease, nonalcoholic steatohepatitis and type II diabetes mellitus.

30 Claims, 7 Drawing Sheets

(56) References Cited

U.S. PATENT DOCUMENTS

| | | |
|---|---|---|
| 7,666,455 B2 | 2/2010 | Resurreccion et al. |
| 8,481,593 B2 | 7/2013 | Okombi |
| 9,089,499 B2 | 7/2015 | Okombi |
| 9,227,898 B2 | 1/2016 | Boue et al. |
| 10,334,689 B2 | 6/2019 | Brebenel |
| 10,334,869 B2 | 7/2019 | Collins et al. |
| 11,173,136 B2 | 11/2021 | Chae |
| 11,382,880 B2 | 7/2022 | Chae et al. |
| 2003/0152682 A1 | 8/2003 | Ley |
| 2004/0198656 A1 | 10/2004 | Najib et al. |
| 2004/0234657 A1 | 11/2004 | Rowley et al. |
| 2007/0183996 A1 | 8/2007 | Okombi |
| 2008/0132544 A1 | 6/2008 | Kitano |
| 2009/0324761 A1 | 12/2009 | Khoo et al. |
| 2015/0361455 A1 | 12/2015 | Katz et al. |
| 2019/0375705 A1 | 12/2019 | Chae et al. |
| 2022/0061370 A1 | 3/2022 | Chae et al. |
| 2022/0062207 A1 | 3/2022 | Chae |
| 2022/0296542 A1 | 9/2022 | Chae |

FOREIGN PATENT DOCUMENTS

| | | | |
|---|---|---|---|
| EP | 1774955 A2 * | 4/2007 | ............... A61K 8/34 |
| GB | 2431876 | 5/2007 | |
| JP | 2012-149004 | 8/2012 | |
| JP | 5207341 B2 | 6/2013 | |
| KR | 2005/0091116 | 9/2005 | |
| KR | 2013-0104240 | 9/2013 | |
| KR | 10-2014-0142580 | 12/2014 | |
| KR | 10-2018-0075425 | 7/2018 | |
| WO | WO 03/097078 | 11/2003 | |
| WO | WO 04/007429 | 1/2004 | |
| WO | WO 04/101757 | 11/2004 | |
| WO | WO 08/154083 | 12/2008 | |
| WO | WO 13/160811 | 10/2013 | |
| WO | WO 18/161077 | 9/2018 | |

OTHER PUBLICATIONS

Chang (Planta Med 2006; 72(14): 1344-1347) (Year: 2006).*

Ahn et al., Hepatocyte Nuclear Factor 4α in the Intestinal Epithelial Cells Protects Against Inflammatory Bowel Disease, Inflammatory Bowel Diseases, 14(7, pp. 908-920, (2008).

Al-Taweel et al., 2012, Bioactive Phenolic Amides from Celtis Africana, Molecules, 17:2675-2682.

Amaro et al., 2014, Hypoglycemic and hypotensive activity of a root extract of Smilax aristolochiifolia, standardized on N-transferuloyl-lyramine, Molecules, 19:11366-11384.

Amin et al., 2006, The Protective Effect of Tribulus terrestris in Diabetes, Ann. NY Acad. Sci 1084:391-401.

Appert et al., 1994, Structural and catalytic properties for the four phenylalanine ammonia-lyase isoenzymes from parsley (petroselinum crispum Nym.), Eur. J. Biochem. 225:491-499.

Ausubel et al., 1987, In Current Protocols in Molecular Biology, Wiley-Interscience (TOC).

Babeu et al., 2014, Hepatocyte Nuclear Factor 4-Alpha Involvement in Liver and Intestinal Inflammatory Networks, World Journal of Gastroenterology, 20(1):22-30.

Baez-Viveros et al., 2004, Metabolic engineering and protein directed evoution increase the yield of L-phenylalanine synthesized from glucose in *Escherichia coli*, Biotechnol. Bioeng. 87:516-524.

Bandoni et al., 1968, Phenylalanine and tyrosine ammonia-lyase activity in some basidiomycetes, Phytochemistry 7: 205-207.

Becker et al., 1991, High-efficiency transformation of yeast by electroporation, in Guthrie ed., Methods in Enzymology, 194:186-187.

Berry, 1996, Improving production of aromatic compounds in *Escherichia coli* by metabolic engineering, Trends Biotechnol. 14:250-256.

Bongaerts et al., 2001, Metabolic engineering for microbial production of aromatic amino acids and derived compounds, Metab. Eng. 3:289-300.

Bradford, 1976, A rapid and sensitive method for the quantitation of microgram quantities of protein utilizing the principle of protein-dye binding, Anal. Biochem. 72:248-254.

Braus, Sep. 1991, Aromatic amino acid biosynthesis in the yeast saccharaomyces cerevisiae: a model system for the regulation of a eukaryotic biosynthetic pathway, Microbiol Rev. 55:349-370.

Bruning et al., 2000, Role of Brain Insulin Receptor in Control of Body Weight and Reproduction, Science, 289:.2122-2125.

Brunt et al., 1999, Nonalcoholic Steatohepatitis: A Proposal for Grading and Staging the Histological Lesions, The American Journal of Gastroenterology, 94(9):2467-2474.

Butler et al., 2000, A Unique Metabolic Syndrome Causes Obesity in the Melanocortin-3 Receptor-Deficient Mouse, Endocrinology, 141(9):3518-3521.

Cai et al., 2006, Peptide deformylase is a potential target for anti-Helicobacter pylori drugs: Reverse docking, enzymatic assay, and X-ray crystallography validation, Protein Science, 15:2071-2081.

Cantos et al., 2000, Effect of postharvest ultraviolet irradiation on resveratrol and other phenolics on Cv. Napoleon table grapes, J. Agric. Food Chem. 48:4606-4612.

Carmiel-Haggai et al., 2005, A High-Fat Diet Leads to the Progression of Non-Alcoholic Fatty Liver Disease in Obese Rats, The FASEB Journal, 19(1):136-138.

Cattin et al., 2009, Hepatocyte Nuclear Factor 4α, a Key Factor for Homeostasis, Cell Architecture, and Barrier Function of the Adult Intestinal Epithelium, Molecular and Cellular Biology, 29(23):6294-6308.

Chahar et al., 2014, Chromatin Profiling Reveals Regulatory Network Shifts and a Protective Role for Hepatocyte Nuclear Factor 4a during Colitis, Molecular and Cellular Biology, 34(17):3291-3304.

Chatzigeorgiou et al. 2009, The Use of Animal Models in the Study of Diabetes Mellitus, In Vivo, 23:245-258.

Chen et al., 2000, Inactivation of the Mouse Melanocortin-3 Receptor Results in Increased Fat Mass and Reduced Lean Body Mass, Nature Genetics, 26(1):97-102.

Chen et al., Mar. 4, 2012, The isolation and identification of two compounds with predominant radical scavenging activity in hempseed, Food Chemistry, 134(2):1030-1037.

Chiba et al., 2003, Hepatocyte Nuclear Factor (HNF)-4alpha Triggers Formation of Functional Tight Junctions and Establishment of Polarized Epithelial Morphology in F9 Embryonal Carcinoma Cells, Experimental Cell Research, 286(2):288-297.

Chiba et al., 2006, The Nuclear Receptor Hepatocyte Nuclear Factor 4a Acts as a Morphogen to Induce the Formation of Microvilli, Journal of Cell Biology, 175(6):971-980.

Cho et al., Jan. 1, 2011, Study on the hypochlolesterolemic and antioxidative effects of tyramine derivatives from the root bark of Lycium chenes Miller, Nutrition Research and Practice, 5(5):412-420.

Choi et al., 2009, Increased production of S-adenysol-L-methionine using recombinant *Saccharomyces cerevisiae* sake K6, Korean J. Chem. Eng. 26(1):156-159.

Clegg et al., 2011, Consumption of a High-Fat Diet Induces Central Insulin Resistance Independent of Adiposity, Physiology & Behavior, 103(1):10-16.

Darsigny et al., 2009, Loss of Hepatocyte-Nuclear-Factor-4α Affects Colonic Ion Transport and Causes Chronic Inflammation Resembling Inflammatory Bowel Disease in Mice, PLoS One, 4(10):e7609.

Davison et al., 2017, Microbiota Regulate Intestinal Epithelial Gene Expression by Suppressing the Transcription Factor Hepatocyte Nuclear Factor 4 Alpha, Genome Research, 27:1195-1206.

Deaner et al., 2017, Systematic testing of enzyme perturbation sensitivities via graded dCas9 modulation in *Saccaromyces cerevisiae*, Metab. Eng. 40:14-22.

Deshpande, 1992, Ethanol production from cellulose by coupled saccharification/fermentaion using *Saccharomyces cerevisiae* and cellulase complex from Scherotium rolfsii UV-8 mutant, Appl. Biochem. Biotechnol., 36:227-234.

Douglas, 1996, Phenylpropanoid metabolism and lignin biosynthesis: from weeds to trees, Trends Plant Sci 1:171-178.

(56) References Cited

OTHER PUBLICATIONS

Drel et al., 2006, The Leptin-Deficient (ob/ob, Mouse: A New Animal Model of Peripheral Neuropathy of Type 2 Diabetes and Obesity, Diabetes, 55(12):3335-3343.
Ehlting et al., 1999, Three 4-coumarate:coenzyme A ligases in Arabidopsis thaliana represent two evolutionarily divergent classes in angiosperms, The Plant Journal 19(1):9-20.
Eichholz et al., 2011, UV-B-induced changes of volatile metabolites and phenolic compounds in blueberries (*Vaccimium corymbosum* L.), Food Chem. 126:60-64.
Ernes et al., 1970, Partial purification and properties of L-phenylalanine ammonia-lyase from streptomyces verticillatus, Can. J. Biochem. 48:613-622.
Engels et al., 2018, Inhibition of Pro-Inflammatory Functions of Human Neutrophils by Constituents of Melodorum fruticosum Leaves, Chemistry & Biodiversity, 15:1-14.
Figlewicz et al., 1986, Brain Insulin Binding is Decreased in Wistar Kyoto Rats Carrying the 'fa' Gene, Peptides, 7(1):61-65.
Galanie et al., Sep. 4, 2015, Complete biosynthesis of opioids in yeast, Science, 349(6252):1095-1100.
Geisel et al., 2003, The Impact of Hyperhomocysteinemia as a Cardiovascular Risk Factor in the Prediction of Coronary Heart Disease, Clinical Chemistry and Laboratory Medicine, 41(11):1513-1517.
Gupta et al., 2005, The MODY1 Gene HNF-4alpha Regulates Selected Genes Involved in Insulin Secretion, Journal of Clinical Investigation, 115(4):1006-1015.
Hagel et al., 2005, Elevated tyrosine decarboxylase and tyramine hydroxycinnamoyltransferase levels increase wound-induced tyramine-derived hydroxycinnamioc acid amide accumulation in transgenic tobacco leaves, Planta, 221:904-914.
Hanson et al., 1981, Phenylalanine ammonia-Lyase, Biochem. Plants, 7:577-625.
Hanson et al., 1972, The enzymic elimination of ammonica, in The Enzymes (3rd ed., Boyer Ed., Academic: New York) pp. 75-167.
Hariri et al., 2010, High-Fat Diet-Induced Obesity in Animal Models, Nutrition Research Reviews, 23(2):270-299.
Havir et al., 1971, L-phenylalanine ammonia-lyase (Maize), Plant Physiol. 48:130-136.
Hayhurst et al., 2001, Hepatocyte Nuclear Factor 4α (Nuclear Receptor 2A1, Is Essential for Maintenance of Hepatic Gene Expression and Lipid Homeostasis, Molecular and Cellular Biology, 21(4):1393-1403.
Hodgins, May 10, 1971, Yeast phenylalanine ammonia-lyase, J. Biol. Chem. 246(9):2977-2985.
Hohlfeld et al., 1995, Partial purification and characterization of hydroxycinnamoyl-coenzyme a:tyramine hydroxycinnamoyltransferase from cell suspension cultures of solanum tuberosum, Plant Physiol. 107:545-552.
HUMMEL at al., 1972, The Influence of Genetic Background on Expression of Mutations at the Diabetes Locus in the Mouse. I. C57BL-KsJ and C57BL-6J Strains, Biochemical Genetics, 7(1):1-13.
Huszar et al., 1997, Targeted Disruption of the Melanocortin-4 Receptor Results in Obesity in Mice, Cell, 88(1):131-141.
Huyskens-Keil et al., 2007, UV-B induced changes of phenol composition and antioxidant activity in black currant fruit (*Ribes nigrum* L.), J. Appl. Bot. Food Qual. 81:140-144.
Ikeda et al., 2006, Towards bacterial strains overproducing L-tryptophan and other aromatics by metabolic engineering, Appl. Microbial. Biotechnol. 69:615-626.
Inoue et al., 2002, Defective Ureagenesis in Mice Carrying a Liver-specific Disruption of Hepatocyte Nuclear Factor 4α (HNF4α, HNF4α Regulates Ornithine Transcarbamylase In Vivo*, The Journal of Biological Chemistry, 277:25257-252625.
Jiang et al., 2003, Expression and Localization of P1 Promoter-Driven Hepatocyte Nuclear Factor-4α (HNF4α, Isoforms in Human and Rats, Nuclear Receptor, 1:1-12.
Joost, 2010, The Genetic Basis of Obesity and Type 2 Diabetes: Lessons from the New Zealand Obese Mouse, a Polygenic Model of the Metabolic Syndrome, Results and Problems in Cell Differentiation, 52:1-11.
Kang et a., 2009, Production of plant-specific tyramine derivatives by dual expression of tyramine N-hydroxycinnamoyltransferase and 4-coumarate:coenzyme A ligase in *Escherichia coli*, Biotechnol Lett, 31:1469-1475.
Keller et al., 1996, Changes in the accumulation of soluble and cell wall-bound phenolics in elicitor-treated cell suspension cultures and fungus-infected leaves of solanum tuberosum, Phytochemistry 42:389-396.
Kennedy et al., 2010, Mouse Models of the Metabolic Syndrome, Disease Models & Mechanisms, 3(3-4):156-166.
Kikuchi et al., Feb. 1997, Mutational analysis of the feedback sites of phenylalanine-sensitive 3-Deoxy-d-arabino-heptulosonate-7-phosphase synthase of *Escherichia coli*, Appl. Environ. Microbiol. 63(2)761-762.
King et al., 2005, Characterization of Cross-Linked Hydroxycinnamic Acid Amides Isolated from Potato Common Scab Lesions, Phytochemistry, 66(20):2468-2473.
King, 2012, The Use of Animal Models in Diabetes Research, British Journal of Pharmacology, 166(3):877-894.
Kiselyuk et al., 2010, Phenothiazine neuroleptics signal to the human insulin promoter as evealed by a novel high-throughput screen, J Biomol. Screen 15(6):663-670.
Kiselyuk et al., 2012, HNF4α Antagonists Discovered by a High-Throughput Screen for Modulators of the Human Insulin Promoter, Chem Biol 19(7):806-818.
Kitahata et al., 1989, Production of Rubusoside Derivatives by Transgalactosylation of Various β-Galactosidases, Agricultural and Biological Chemistry, 53:.2923-2928.
Kleiner et al., 2005, Design and Validation of a Histological Scoring System for Nonalcoholic Fatty Liver Disease, Hepatology, 41(6):1313-1321.
Knobloch et al., 1977, 4-Coumarate:CoA ligase from cell suspension cultures of Petroselinum hortense Hoffm., Arch. Biochem. Biophys. 184:237-248.
Ko et al. 2015, N-trans-p-caffeoyl tyramine isolated from Tribulus terrestris exerts anti-inflammatory effects in lipopolysaccharide-stimulated RAW 264.7 cells International Journal of Molecular Medicine, 36:1042-1048.
Koopman et al., 2012, Do novo production of the flavonoid naringenin in engineered *Saccharomyces cerevisiae*, Microb. Cell Fact. 11:155.
Koukol et al., Oct. 1961, The metabolism of aromatic compounds in higher plants, J. Biol. Chem. 236(10):2692-2698.
Lee et al., 1996, Two divergent members of a tobacco 4-coumarate:coenzyme A Ligase (4CL, gene family, Plant Physiol. 112:193-205.
Lee et al., 2013, Reversal of Lipotoxic Effects on the Insulin Promoter by Alverine and Benfluorex: Identification as HNF4a Activators, ACS Chem Biol 8(8):1730-1736.
Lee et al., 2017, Anti-inflammatory effect of tribulusamide D isolated from Tribulus terrestris in lipopolysaccharide-stimulated RAW264.7 macrophages, Molecular Medicine Report, 16:4421-4428.
Lee et al., 2021, Liver fat storage is controlled by HNF4α through induction of lipophagy and is reversed by a potent HNF4αagonist Cell Death & Disease, 2021, 18 pages.
Leiter et al., 2004, Differential Levels of Diabetogenic Stress in Two New Mouse Models of Obesity and Type 2 Diabetes, Diabetes, 53(Suppl 1):S4-S11.
Leiter, 2009, Chapter 1: Selecting the Right Mouse Model for Metabolic Syndrome in Type 2 Diabetes Research: Methods in Molecular Biology, 560:1-17.
Leung et al., Aug. 1989, A method for random mutagenesis of a defined DNA segment using a modified polymerase chain reaction, Technique, 1(1):11-15.
Levin et al., 1997, Selective Breeding for Diet-Induced Obesity and Resistance in Sprague-Dawley Rats, American Journal of Physiology, 273:R725-730.

(56) References Cited

OTHER PUBLICATIONS

LOBOV et al., 1991, Enzymic Production of Sweet Stevioside Derivatives: Transglucosylation by glucosidases, Agricultural and Biological Chemistry, 55(12):2959-2965.

Lovdal et al., 2010, Synergetic effects of nitrogen depletion, temperature, and light on the content of phenolic compounds and gene expression in leaves of tomato, Phytochemistry 71:605-613.

Ludidi et al., May 15, 2015, The Intestinal Barrier in Irritable Bowel Syndrome: Subtype-Specific Effects of the Systemic Compartment in an in Vitro Model, PLoS One, 10(5):e0123498.

Ludwig et al., 1980, Nonalcoholic Steatohepatitis: Mayo Clinic Experiences With a Hitherto Unnamed Disease, Mayo Clinic Proceedings, 55(7):434-438.

Lutke-Eversloh et al., 2008, Combinatorial pathway analysis for improved L-tyrosine production in *Eschericia coli*: identification of enzymative bottlenecks by systematic gene overexpression, Metabolic Engineering 10:68-77.

Luttik et al., 2008, Alleviation of feedback inhibition in saccharomyces cerevisiae aromatic amino acid biosynthesis: quantification of metabolic impact, Metab. Eng. 10:141-153.

Maciel et al., 2016, New Alcamide and Anti-oxidant Activity of Pilosocereus gounellei A. Weber ex K. Schum. Bly. Ex Rowl. (Cactaceae), Molecules, 21:1-13.

Mao et al., 2017, Combinatorial analysis of enzymatic bottlenecks of L-tyrosine pathway by p-coumaric acid production in *Saccharamyces cerevisiae*, Biotechnol. Lett. 39(7):977-982.

Martinez-Jimenez et al., 2010, Hepatocyte Nuclear Factor 4α Coordinates a Transcription Factor Network Regulating Hepatic Fatty Acid Metabolism, Molecular and Cellular Biology, 30(3):565-577.

Matsuoka et al., 2015, Preserving Mafa Expression in Diabetic Islet β-cells Improves Glycemic Control in Vivo, Journal of Biological Chemistry, 290(12):7647-7657.

MILLAR et al., 2005, Determining hepatic Triglyceride Production in Mice:Comparison of Poloxamer 407 with Triton WR-1339, Journal of Lipid Research, 46:2023-2028.

Miller et al., 1987, Production of phenylalanine and organic acids by phosphoenolpyruvate carboxylase-dificient mutants of *Escherichia coli*, J. Ind. Microbiol. 2:143-149.

Mul et al., 2011, Melanocortin Receptor 4 Deficiency Affects Body Weight Regulation, Grooming Behavior, and Substrate Preference in the Rat, Obesity, 20(3):612-621.

Negrel et al., 1993, Wound-induced tyramine hydroxycinnamoyl transferase in potato (Solanum tuberosum) tuber discs, J. Plant Physiol. 142(5):518-524.

Negrel et al., 1995, Induction of phenylpropanoid and tyramine metabolism in pectinase- or pronase-elicited cell suspension cultures of tobacco (Nicotiana tabacum), Physiol. Plant. 95:569-574.

Nelms et al., Aug. 1992, Novel mutations in the pheA gene of *Escherichia coli* K-12 which result in highly feedback inhibition-resistant variants of chorismite mutase/prephenate dehydratase, Appl. Environ. Microbiol. 58(8):2592-2598.

Neuschwander-Tetri et al., 2003, Nonalcoholic Steatohepatitis: Summary of an AASLD Single Topic Conference, Hepatology, 37(5):1202-1219.

Nijkamp et al., 2005, The solvent-tolerant Pseudomonas putida S12 as host for the production of cinnamic acid from glucose, Appl. Microbiol. Biotechnol. 69:170-177.

Nijkamp et al., 2007, Optimization of the solvent-tolerant Pseudomonas putida S12 as host for the production of p-coumarate from glucose, Appl. Microbiol. Biotechnol. 74:617-624.

Nishioka et al., 1997, Isolation and activity of N-p-coumaroyltyramine, an a-Jlucosidase inhibitor in welsh onion {Allium fislulosum), Biosci. Biotechnol. Biochem. 61 (7):1138-1141.

Ogata et al., 1967, Metabolism of aromatic amino acid in microorganisms, Agric. Biol. Chem. 31(2):200-206.

Okayasu et al., 1990, A Novel Method in the Induction of Reliable Experimental Acute and Chronic Ulcerative Colitis in Mice, Gastroenterology, 98(3):694-702.

Olson et al., 2007, Production of tyrosine from sucrose or glucose achieved by rapid genetic changes to phenylalanine-producing *Escherichia coli* strains, Appl. Microbiol. Biotechnol. 74(5):1031-1040.

Paiva et al., 1984, IacZ fusions to genes that specify exported proteins: a general technique, Nol. Gen Genet, 194:388-394.

Park et al., 2009, Endosperm-specific expression oftyramine N-hyroxycinnamoyltransferase and tyrosine decarboxylase from a single self-processing polypeptide produces high levels of tyramine derivatives in rice seeds, Biotechnol. Lett. 31(6):911-915.

Park, 2007, Caffedymine from cocoa has cox inhibitory activity suppressing the expression of a platelet activation marker, P-selectin, J. Agric. Food Chem, 55:2171-2175.

Parviz et al., 2003, Hepatocyte Nuclear Factor 4alpha Controls the Development of a Hepatic Epithelium and Liver Morphogenesis, Nature Genetics, 34(3):292-296.

Patnaik et al., Nov. 1994, Engineering of *Escherichia coli* central metabolism for aromatic metabolite production with near theoretical yield, Appl. Environ. Microbiol., 60(11):3903-3908.

Peddibhotla et al., 2013, Discovery of ML314, a Brain Penetrant Nonpeptidic β-Arrestin Biased Agonist of the Neurotensin NTR1 Receptor, ACS Medicinal Chemistry Letters, 4(9):pp. 846-851.

Porter et al., 1999, Functional characterization of agonists at recombinant human 5-HT2A, 5-HT2B and 5-HT2C receptors in CHO-K1 cells, Br J. Pharmacol. 128(1):13-20.

PubChem-CID-88222313, Create Date: Feb. 12, 2015, 9 pp.

PubChem-pccompound-CID 54408305, Create Date Dec. 4, 2011, pp. 1-24.

PubChem-pccompound-selected items 1-14, Create Date Mar. 26, 2005 to Aug. 6, 2016, 3 pp.

Qin et al., 2018, An obesity-associated gut microbiome reprograms the intestinal epigenome and leads to altered colonic gene expression, Genome Biol. 19:7.

Rodriguez et al., 2015, Establishment of a yeast platform strain for production of p-coumaric acid through metabolic enGineering of aromatic amino acid biosynthsis, MetAbolic Engineering, 31:181-188.

Rogers et al., 1984, Meal Patterns and Food Selection During the Development of Obesity in Rats Fed a Cafeteria Diet, Neuroscience & Biobehavioral Reviews, 8(4):441-453.

Roje et al., Feb. 8, 2002, Metabolic engineering in yeast demonstrates that S-adenosylmethionine controls flux through the methylenetetrahydrofolate reductase reaction in vivo, J. Biol. Chem. 277:4056-4061.

Rosler et al., 1997, Maise phenylalanine ammonia-lyase has tyrosine ammonia-lyase activity, Plant Physiol. 113:175-179.

Sambrook et al., 1989, Molecular Cloning: A Laboratory Manual, 2nd ed., Cold Spring Harbor Laboratory, Cold Spring Harbor, NY (TOC).

Sanders et al., 2016, De Novo Lipogenesis in the Liver in Health and Disease: More Than just a Shunting Yard for Glucose, Biological reviews of the Cambridge Philosophical Society, 91(2):452-468.

Savage, 2009, Mouse Models of Inherited Lipodystrophy, Disease Models & Mechanisms, 2(11-12):554-562, (2009).

Schmidt et al., 1998, Elicitor-stimulated biosynthesis of hydroxycinnamoyltyramines in cell suspension cultures of Solanum tuberosum, Planta, 205:51-55.

Schmidt et al., Feb. 12, 1999, Cloning and expression of a potato cDNA encoding hydroxycinnamoyl-CoA:Tyramine N-(Hydroxycinnamoyl)transferase, J. Biol. Chem. 274(7):4273-4280.

Schmidt et al., Mar. 21, 2014, Assessment of constituents inAlliumby multivarate data analysis, high-resolution α-glucosidase inhibition assay and HPLC-SPE, Food Chemistry, 161:192-198.

Shepherd et al., 1993, Adipose Cell Hyperplasia and Enhanced Glucose Disposal in Transgenic Mice Overexpressing GLUT4 Selectively in Adipose Tissue, Journal of Biological Chemistry, 268:.22243-22246.

Shiota et al., 2012, Diabetes in Zucker Diabetic Fatty Rat, Methods in Molecular Biology, 933:103-123.

Sim et al., 2015, Bacterial synthesis of N-hydroxycinnamoyl phenethylamines and tyramines, Microbial Cell Fact. 14:162.

(56) References Cited

OTHER PUBLICATIONS

Spath et al., 1998, Hepatocyte Nuclear Factor 4 Provokes Expression of Epithelial Marker Genes, Acting As a Morphogen in Dedifferentiated Hepatoma Cells, Journal of Cell Biology, 140(4):935-946.
Spee et al., 1993, Efficient random mutagenesis method with adjustable mutation frequency by use of PCR and diTP, Nucl. Acids Res. 21(3):777-778.
Sprenger et al., 2007, From scratch to value: engineering *Escherichia coli* wild type cells to the production of L-phenylalanine and other fine chemicals derived from chorismate, Appl. Microbial. Biotechnol. 75:739-749.
Stenman et al., 2012, High-Fat-Induced Intestinal Permeability Dysfunction Associated with Altered Fecal Bile Acids, World Journal of Gastroenterology, 18(9):923-929.
Tatarko et al., 2001, Disruption of a global regulatory gene to enhance central carbon flux into phenylalanine biosynthesis in *Escherichia coli*, Curr. Microbiol. 43:26-32.
Traini et al., 2016, Changes of Excitatory and Inhibitory Neurotransmitters in the Colon of Rats Underwent to the Wrap Partial Restraint Stress, Neurogastroenterology & Motility, 28(8):1172-1185.
Traini et al., 2017, Repeated Otilonium Bromide Administration Prevents Neurotransmitter Changes in Colon of Rats Underwent to Wrap Restraint Stress, Journal of Cellular and Molecular Medicine, 21:735-745.
Trenchard et al., 2015, De novo production of the key branch point benzylisoquinoline alkaloid reticuline in yeast, Metab. Eng. 31:74-83.
Tschop et al., 2001, Rodent Obesity Models: An Overview, Experimental and Clinical Endocrinology & Diabetes, 109(6)307-319.
Villegas et al., 1990, Elicitor-induced hydroxycinnamoyl-CoA:tyramine hydroxycinnamoyltransferase in plant cell suspension cultures, Physiol. Plant. 78:414-420.
Wang et al., 2014, Leptin- and Leptin Receptor-Deficient Rodent Models: Relevance for Human Type 2 Diabetes, Current Diabetes Reports, 10(2):131-145.
Wang et al., 2017, Identification and Quantification of Potential Anti-inflammatory Hydroxycinnamic Acid Amides from Wolfberry, Journal of Agricultural and Food Chemistry, 65:364-372.
Wang et al., Mar. 25, 1994, Functional characterization of a unique liver gene promoter, J. Biol. Chem. 269(12):9137-9146.
Williams et at., 1988, Stress-Induced Changes in Intestinal Transit in the Rat: A Model for Irritable Bowel Syndrome, Gastroenterology, 94(3):611-621.
Yakandawala et al., 2008, Metabolic engineering of *Escherichia coli* to enhance phenylalanine production, Appl. Microbiol. Biotechnol. 78:283-291.
Yamamoto et al., 1994, Effective Production of Glycosyl-Steviosides by Alpha-1,6 Transglucosylation of Dextrin Dextranase, Bioscience, Biotechnology, and Biochemistry, 58(9):1657-1661.
Yaswen et al., 1999, Obesity in the Mouse Model of Pro-Opiomelanocortin Deficiency Responds to Peripheral Melanocortin, Nature Medicine, 5(9):1066-1070.
Yeh, Aug. 2004, C-reactive Protein is an Essential Aspect of Cardiovascular Risk Factor Stratification, The Canadian Journal of Cardiology, 20(Suppl B):93B-96B.
Yi et al., 2003, Altered glucose transport and shikimate pathway product yields in *E. coli*, Biotechnol. Prog. 19:1450-1459.
Yin et al., Hepatic HNF4α Is Essential for Maintaining Triglyceride and Cholesterol Homeostasis, Arteriosclerosis, Thrombosis, and Vascular Biology, 31(2, pp. 328-336, (2011).
Zacares et al., 2007, Induction of p-Coumaroyldopamine and feruloyldopamine, two novel metabolites, in tomato by the bacterial pathogen Pseudomonas syringae, Mol. Plant Microbe Interact. 20(11):1439-1448.
Zhao et al., Feb. 1994, Pseudomonas aeruginosa possesses homologues of mammalian phenylalanine hydroxylase and 4α-carbinolamine dehydratase/DCoH as part of a three-component gene cluster, Proc. Natl. Acad. Sci. USA. 91:1366-1370.
Zhou et al., 1991, Random mutagenesis of gene-sized DNA molecules by use of PCR with Taq DNA polymerase, Nucleic Acids Res. 19(21):6052-6052.
International Search Report and Written Opinion in PCT/US2019/012993 dated Apr. 9, 2019.
Extended European Search Report dated Oct. 29, 2021 in patent application No. 19738536.2.
Back et al., 2001, Cloning and characterization of a hydroxycinnamoyl-CoA: tyramine N-(hydroxycinnamoyl) transferase induced response to UV-C and wounding from capsicum annum, Plant Cell Physiol, 42(5):475-481.
Ishihara et al., 2000, Induction of N-hydroxycinnamoyltyranine synthesis and tyramine N-hydroxycinnamoyltransferase (THT) activity by wounding in maize leaves, BioSci. Beiotechnol. Biochem, 65(5):1025-1031.
Kim et al., 2018, Portulaca oleracea extracts and their active compounds ameriliorate imflammatory bowel diseases in vitor and in vivo by modulating TNF-α, IL-6 and IL-13 signalling, Food Research International, 106:335-343.
Macoy et al., 2015, Biotic stress related functions of hydroxycinnamic acid amide in plants, J. Plant Biol., 58:156-163.
Pang et al., 2007, Polyamines, all-purpose players in response to environment stresses in plants, Plant Stress, 1(2):173-188.
Bolster et al., Dec. 30, 2022, Impact of Selected Plant Bioactives on Improvement of Impaired Gut Barrier Function using Human Primary Cell Intestinal Epithelium, J. Food Bioactives, https://doi.org/10.31665/JFB.2022.18324.

\* cited by examiner

METHOD FOR MODULATING METABOLISM

CROSS-REFERENCE TO RELATED APPLICATIONS

This application is a continuation of U.S. application Ser. No. 17/501,230 filed Oct. 14, 2021, which is a continuation of U.S. application Ser. No. 16/961,035, filed on Jul. 9, 2020, issued Nov. 16, 2021 as U.S. Pat. No. 11,173,136, which was the National Phase of International Application No. PCT/US2019/012993, filed on Jan. 10, 2019 and published on Jul. 18, 2019, as WO 2019/140052, which claims the benefit of priority of U.S. Provisional Application No. 62/615,671 filed Jan. 10, 2018, the content of which is incorporated herein by reference in its entirety.

BACKGROUND

The "Western Diet" has been associated with a global rise in metabolic disorders such as obesity, type II diabetes mellitus (T2DM), metabolic syndrome, nonalcoholic fatty liver disease (NAFLD), heart disease, and stroke. Interactions between genetic and environmental factors such as diet and lifestyle, particularly over-nutrition and sedentary behavior, promote the progression and pathogenesis of these polygenic diet-related diseases. Their current prevalence is increasing dramatically to epidemic proportions. Nutrition is probably the most important environmental factor that modulates expression of genes involved in metabolic pathways and the variety of phenotypes associated with obesity, the metabolic syndrome, and type II diabetes mellitus. Furthermore, the health effects of nutrients may be modulated by genetic variants.

A 70% ethyl alcohol extract of *Tribulus terrestris* has been suggested to provide a protective effect in a model of type I diabetes mellitus (i.e., streptozotocin-induced diabetic rats) by inhibiting oxidative stress (Amin, et al. (2006) *Ann. NY Acad. Sci.* 1084:391-401).

U.S. Pat. Nos. 8,481,593 and 9,089,499 disclose para-coumaric acid derivatives such as N-trans-feruloyltyramine in topical and cosmetic compositions for use in inhibiting human tyrosinase and in the treatment of hyperpigmentation.

An acetone extract from *Smilax aristolochiifolia* root, which is enriched for N-trans-feruloyltyramine, has been suggested to be useful in counteracting some symptoms (e.g., hypertriglyceridemia, insulin resistance, blood pressure, and inflammation) in an injury model associated with metabolic syndrome (Amaro, et al. (2014) *Molecules* 19:11366-84).

US 2008/0132544 suggests the use of isolated N-trans-feruloyl tyramine from *Piper nigrum* in a composition for the treatment of visceral fat obesity, T2DM, insulin resistant syndrome and metabolic syndrome.

SUMMARY OF THE INVENTION

The present invention provides a method for modulating metabolism by providing to a subject in need thereof a consumable composition composed of at least one carrier and an effective amount of an extract comprising a compound of Formula I, or an isomer, heterodimer, or conjugate thereof:

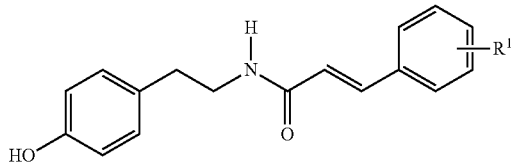

Formula I wherein
$R^1$ is present or absent, and when present is a substituent on one or more ring atoms and is for each ring atom independently a hydroxy group, halo group, substituted or unsubstituted lower alkyl group, or substituted or unsubstituted lower alkoxy group; and
the dashed bond is present or absent.

In some embodiments, the compound has the structure of Formula II:

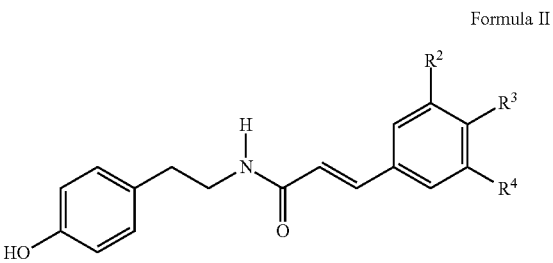

Formula II wherein, $R^2$ is present or absent, and when present is a hydroxy or methoxy group; $R^3$ is present or absent, and when present is a hydroxy group; and $R^4$ is present or absent, and when present is a hydroxy or methoxy group.

Preferably, the extract is an ethanol extract of a member of the genus *Allium, Amoracia, Chenopodium, Fagopyrum, Annona, Piper, Eragrostis, Zea, Cannabis, Ipomea, Capsicum, Lycium, Solanum*, or *Tribulus*. In some embodiments, the consumable composition is formulated as a dietary supplement, food ingredient or additive, a medical food, nutraceutical or pharmaceutical composition. Ideally, an effective amount of the composition provides an improvement in HNF4α activity, insulin-like growth factor levels, blood sugar levels, insulin levels, HbA1C levels, C peptide levels, triglyceride levels, free fatty acid levels, blood uric acid levels, microalbuminuria levels, glucose transporter expression, adiponectin levels, total serum cholesterol levels, high density lipoprotein levels, low density lipoprotein levels or a combination thereof. In certain embodiments, the subject has or is at risk of developing a metabolic disorder, e.g., insulin resistance, hyperglycemia, type II diabetes mellitus, obesity, glucose intolerance, dyslipidemia, hypercholesterolemia, hyperlipoproteinemia, hyperinsulinemia, atherosclerotic disease, coronary artery disease, metabolic syndrome, or hypertension.

DETAILED DESCRIPTION OF THE INVENTION

Figure 1:
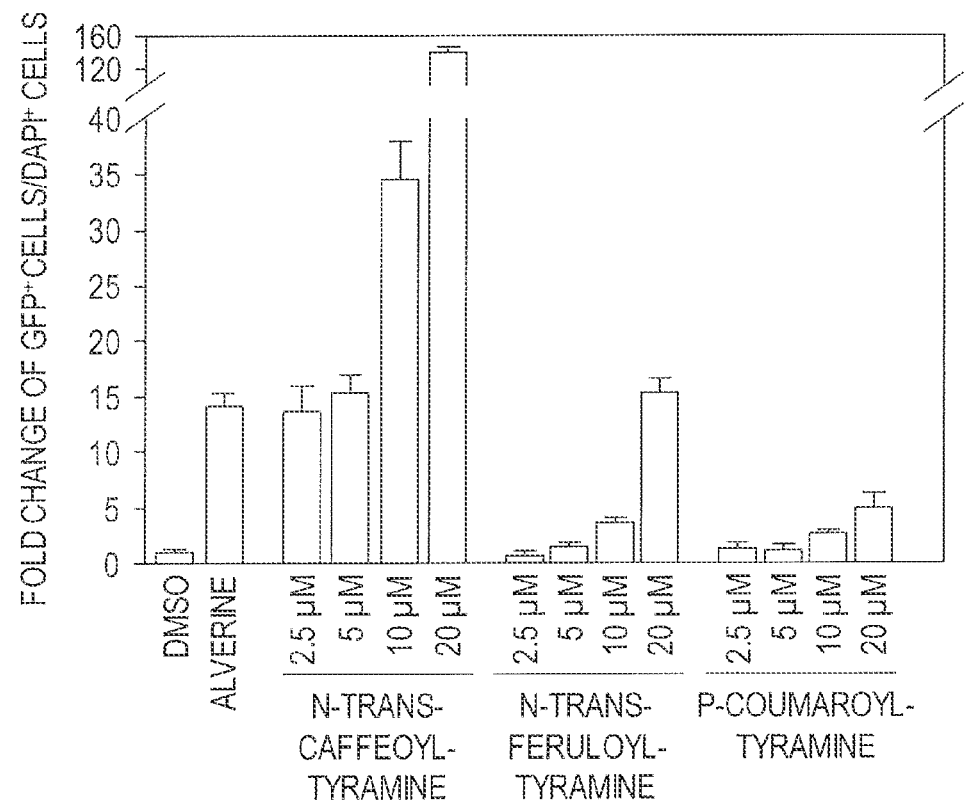
FIG. 1 shows a dose-response analysis of N-trans-caffeoyltyramine, N-trans-feruloyltyramine and p-coumaroyltyramine in an assay measuring insulin promoter activity. Dimethylsulfoxide (DMSO) and alverine (20 μM) were used as negative and positive controls, respectively.

This invention provides tyramine containing hydroxycinnamic acid amides, which modulate metabolism, in particular HNF4α activity, thereby mitigating the adverse effects of free fatty acids in both liver cells and pancreatic β-cells. The tyramine containing hydroxycinnamic acid amide of this invention are analogs of lead compounds identified in traditional screening assays for agents that modulate known signaling pathways. The tyramine containing hydroxycinnamic acid amides exhibit dose-response HNF4α activity, as initially determined in a T6PNE engineered pancreatic cell, and upregulate insulin gene expression. Further, these compounds show strong, lipid clearing activity in a hepatocyte (hepG2) lipid challenge model of fatty liver disease. While not wishing to be bound by theory, it is believed that the tyramine containing hydroxycinnamic acid amides of this invention, modulate HNF4α activity as a result of higher affinity for the HNF4α binding site than the natural ligand, palmitic acid, which down regulates HNF4α activity. Genetic, functional genomic, transcriptomic and clinical evidence indicate that HNF4α agonists can improve overall metabolic health by enabling the body to maintain sugar and lipid homeostasis. Accordingly, the compounds herein are of use in methods of promoting and/or recovering healthy HNF4α function, mitigating the adverse effects of free fatty acids, modulating metabolism, and addressing the underlying pathogenesis of metabolic disorders, such as NAFLD, nonalcoholic steatohepatitis (NASH) and T2DM. Using the composition of this invention, health and well-being are improved and promoted.

Active Compound

This invention provides plant-derived aromatic or more acidic hydroxyl groups arenes, and their use in modulating metabolites attached to with one aromatic metabolism. In one embodiment, the plant-derived aromatic metabolite is a structural analog of compound 1:

Compound 1

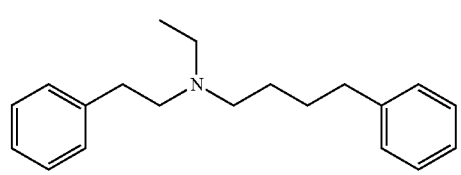

In particular, the invention encompasses a tyramine containing hydroxycinnamic acid amide having the structure of Formula I, or an isomer, salt, homodimer, heterodimer, or conjugate thereof:

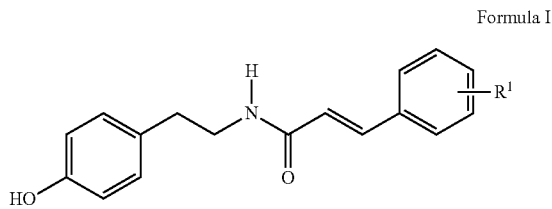

Formula I wherein
$R^1$ is present or absent, and when present is a substituent on one or more ring atoms (e.g., position 2, 3, and/or 4) and is for each ring atom independently a hydroxy group, halo group, substituted or unsubstituted lower alkyl group, or substituted or unsubstituted lower alkoxy group; and
the dashed bond is present or absent.

For the groups herein, the following parenthetical subscripts further define the groups as follows: "$(C_n)$" defines the exact number (n) of carbon atoms in the group. For example, "$C_1$-$C_6$-alkyl" designates those alkyl groups having from 1 to 6 carbon atoms (e.g., 1, 2, 3, 4, 5, or 6, or any range derivable therein (e.g., 3-6 carbon atoms)).

The term "lower alkyl" is intended to mean a branched or unbranched saturated monovalent hydrocarbon radical containing 1 to 6 carbon atoms (i.e., $C_1$-$C_6$-alkyl), such as methyl, ethyl, propyl, isopropyl, tert-butyl, butyl, n-hexyl and the like.

Similarly, a lower alkoxy group is a $C_1$-$C_6$-alkoxy group having the structure —OR wherein R is "alkyl" as defined further above. Particular alkoxy groups include, by way of example, methoxy, ethoxy, n-propoxy, isopropoxy, n-butoxy, tert-butoxy, iso-butoxy, sec-butoxy, n-pentoxy, 1,2-dimethylbutoxy, and the like.

The term "halo" is used herein to refer to chloro (Cl), fluoro (F), bromo (Br) and iodo (I) groups. In particular embodiments, the halo group is a fluoro group.

In any of the groups described herein, an available hydrogen may be replaced with an alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, alkoxyalkoxy, acyl, halo, nitro, cyano, carboxy, alkoxycarbonyl, aryloxycarbonyl, aralkoxycarbonyl, alkyl sulfonyl, aryl sulfonyl, heteroarylsulfonyl, alkylthio, arylthio, heteroarylthio, aralkylthio, heteroaralkylthio, cycloalkyl, or heterocyclyl.

Any undefined valency on an atom of a structure shown in this application implicitly represents a hydrogen atom bonded to the atom.

In some embodiments, $R^1$ is present and preferably represents independent substituents at the para and meta positions. In particular embodiments, $R^1$ is present and represents a hydroxy group at the para position and a hydroxy or lower alkoxy group at the meta position. In certain embodiments, the tyramine containing hydroxycinnamic acid amide having the structure of Formula I is in the trans configuration.

In particular embodiments, the tyramine containing hydroxycinnamic acid amide has a structure of Formula II:

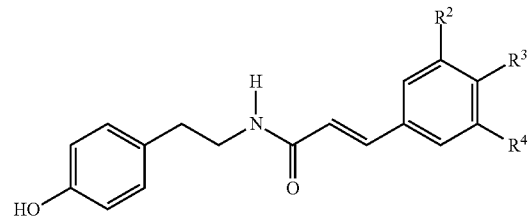

Formula II wherein,
$R^2$ is present or absent, and when present is a hydroxy or methoxy group;
$R^3$ is present or absent, and when present is a hydroxy group; and
$R^4$ is present or absent, and when present is a hydroxy or methoxy group.

"Isomer" refers to especially optical isomers (for example essentially pure enantiomers, essentially pure diastereomers, and mixtures thereof) as well as conformation isomers (i.e., isomers that differ only in their angles of at least one chemical bond), position isomers (particularly tautomers), and geometric isomers (e.g., cis-trans isomers).

In certain embodiments, the tyramine containing hydroxycinnamic acid amide is one of the following compounds:

N-trans-caffeoyltyramine

N-cis-caffeoyltyramine

N-trans-feruloyltyramine

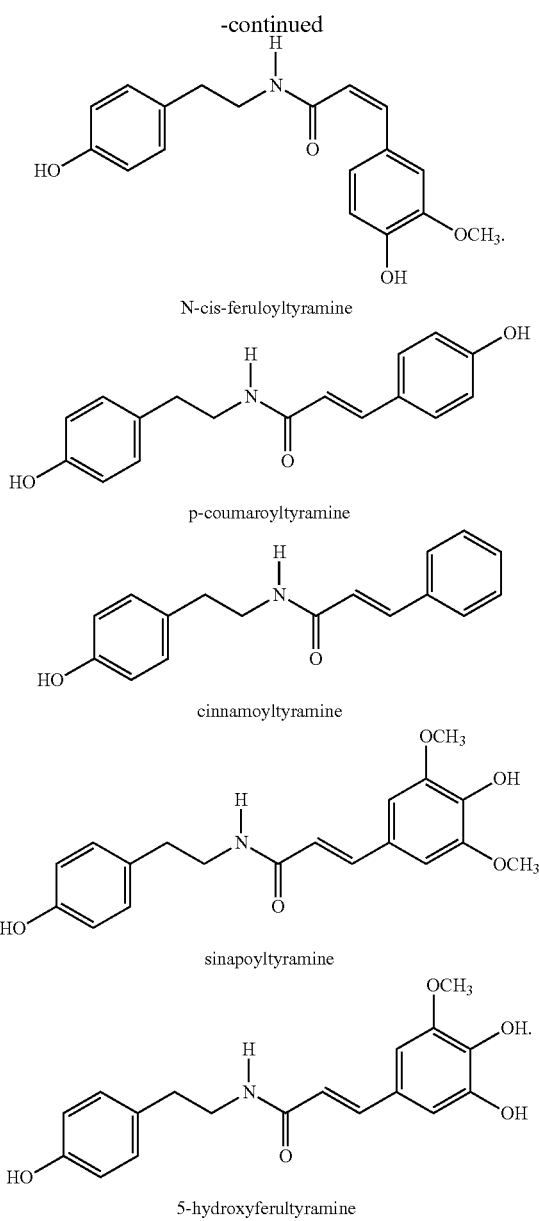

N-cis-feruloyltyramine p-coumaroyltyramine cinnamoyltyramine sinapoyltyramine 5-hydroxyferultyramine A salt of a compound of this disclosure refers to a compound that possesses the desired pharmacological activity of the parent compound and includes: (1) an acid addition salt, formed with an inorganic acid such as hydrochloric acid, hydrobromic acid, sulfuric acid, nitric acid, phosphoric acid, and the like; or formed with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) a salt formed when an acidic proton present in the parent compound is replaced.

As is known in the art, a homodimer is a molecule composed of two identical tyramine containing hydroxycinnamic acid amide subunits. By comparison, a heterodimer is a molecule composed of two different tyramine containing hydroxycinnamic acid amide subunits. Examples of homodimers of this invention include but are not limited to a cross-linked N-trans-feruloyltyramine dimer, a cross-linked N-trans-caffeoyltyramine dimer and a cross-linked p-coumaroyltyramine dimer. See, for example, King & Calhoun (2005) *Phytochemistry* 66(20):2468-73, which teaches the isolation of a cross-linked N-trans-feruloyltyramine dimer from potato common scab lesions. Conjugates of monomers of tyramine containing hydroxycinnamic acid amide and other compounds, such as lignan amides. Examples of conjugates include, but are not limited to cannabisin A, cannabisin B, cannabisin C, cannabisin D, cannabisin E and cannabisin F.

Sources of Active Compound

A compound of this invention can be obtained from any suitable botanical species and/or botanical raw material known to possess a compound of Formula I. Preferably, the compound is provided as an extract comprising the compound or a substantially pure compound.

An "extract" refers to a composition containing a compound of Formula I, which is separated from other unwanted substances present in the natural source material from which the extract was obtained. In some embodiments, the natural source material is a plant. Plant extracts can be obtained from any plant tissue including a whole plant; a plant part such as shoot vegetative organs/structures (for example, leaves, stems and tubers), roots, flowers and floral organs/structures. (for example, bracts, sepals, petals, stamens, carpels, anthers and ovules), a seed (including embryo, endosperm, and seed coat) or fruit (the mature ovary); a plant tissue (for example, vascular tissue, ground tissue, and the like); cells (for example, guard cells, egg cells, and the like), or exudates as well as progeny and cultures or cell lines of the same. Preferably, the extract contains compounds that will be found to be generally recognized as safe (GRAS) for human consumption. Accordingly, in certain embodiments the extract is from an edible source. In this respect, the extract is an edible extract.

Extracts can be prepared by freezing, grinding, macerating, pulverizing, fermenting, percolation, decoction, solvent extraction (e.g., partitioning) or precipitation, treatment with activated charcoal, evaporation, filtration, and/or chromatographic fractionation of the source material of interest. In this respect, an "extract" of the invention can be crude, fractionated, sub-fractionated, separated, isolated, enriched or purified, without being limited thereto. The term "crude" means compounds or molecules that have not been entirely separated from the components of the original composition in which it was present. In embodiments pertaining to fractions or sub-fractions, a molecule in crude extract may be subjected to partial separation to provide a less crude extract containing other substances. In some embodiments, the compound is isolated. The term "isolated" means that a compound or molecule is substantially enriched or purified with respect to the complex cellular milieu in which it naturally occurs, such as in a crude extract. When an isolated molecule is enriched or purified, the absolute level of purity is not critical and those skilled in the art can readily determine appropriate levels of purity according to the use to which the material is to be put. In some circumstances, the isolated molecule forms part of a composition (for example a more or less crude extract containing many other substances), which may for example contain other components. In other circumstances, the isolated molecule may be purified to essential homogeneity, for example as determined spectrophotometrically, by NMR or by chromatography (for example LC-MS).

Suitable solvents for preparing an extract include, e.g., n-pentane, hexane, butane, chloroform, dichloromethane, di-ethyl ether, acetonitrile, water, butanol, isopropanol, ethanol, methanol, glacial acetic acid, acetone, norflurane (HFA134a), ethyl acetate, dimethyl sulfoxide, heptafluoropropane (HFA227), and subcritical or supercritical fluids such as liquid carbon dioxide and water, or a combination thereof in any proportion. When solvents such as those listed above are used, the resultant extract typically contains non-specific lipid-soluble material. This can be removed by a variety of processes including "winterization", which involves chilling to a specified temperature, typically −20° C. followed by filtration or centrifugation to remove waxy ballast, extraction with subcritical or supercritical carbon dioxide or non-polar solvents (e.g., hexane) and by distillation.

Extracts enriched for a compound of the invention are ideally obtained by chromatographic fractionation. Chromatographic fractionation typically includes column chromatography and may be based on molecular sizing, charge, solubility and/or polarity. Depending on the type of chromatographic method, column chromatography can be carried out with matrix materials composed of, for example, dextran, agarose, polyacrylamide, silica, C18, C8, polyvinylpyrrolidone, polystyrene, celite, and phenyl-hexy and can include solvents such as dimethyl sulfoxide, pyridine, water, dimethylformamide, methanol, saline, ethylene dichloride, chloroform, propanol, ethanol, isobutanol, formamide, methylene dichloride, butanol, acetonitrile, isopropanol, tetrahydrofuran, dioxane, chloroform/dichloromethane, methanol, hexane, and ethyl acetate.

Typically, the product of the chromatographic step is collected in multiple fractions, which may then be tested for the presence of the desired compound using any suitable analytical technique (e.g., thin layer chromatography, mass spectrometry, and ultraviolet absorption). Fractions enriched in the desired compound may then be selected for further purification.

As an alternative, or in conjunction with chromatography, crystallization may be performed to obtain high purity tyramine containing hydroxycinnamic acid amides. The solubility of the tyramine containing hydroxycinnamic acid amide is adjusted by changing temperature and/or the composition of the solution, for instance by removing ethanol, and/or adjusting the pH to facilitate precipitation, followed by filtration or centrifugation of the precipitated crystals or oils. Other suitable methods include, but are not limited to, liquid-liquid extraction, centrifugal partition chromatography or adsorption onto a resin or removal of impurities with resin.

A "substantially pure" preparation of a compound is defined as a preparation having a chromatographic purity (of the desired compound) of greater than 95%, more preferably greater than 96%, more preferably greater than 97%, more preferably greater than 98%, more preferably greater than 99% and most preferably greater than 99.5%, as determined by area normalization of an HPLC profile.

The term "extract comprising a compound" encompasses preparations having at least 2%, preferably greater than 5%, more preferably greater than 10% chromatographic purity for the desired compound. Such an extract will generally contain a greater proportion of impurities, non-target materials and other molecules than a "substantially pure" preparation.

In particular embodiments, an "extract comprising a compound" is a "botanical" product or substance. In this context, "botanical" refers to "products that include plant materials, algae, macroscopic fungi and combinations thereof" Botanicals are defined by the process steps used to prepare the extract (e.g., by pulverization, decoction, expression, aqueous and/or ethanol extraction) and provide a quantified amount of one or more of the compounds of interest.

Ideally, a compound of this invention is extracted and/or purified from a plant. Exemplary plants sources include, but are not limited to, plants in the genera, family, order, genus, species listed in Table 1.

TABLE 1

| Order | Family | Genus | Common name |
|---|---|---|---|
| Asparagales | Amaryllidaceae | Allium | Garlic |
| | | | Onion |
| | | | Leek |
| Brassicales | Brassicaceae | Amoracia | Horseradish |
| Caryophyllales | Amaranthaceae | Chenopodium | Quinoa |
| Caryophyllales | Polyconaceae | Fagopyrum | Buckwheat |
| Manoliales | Annonaceae | Annona | Cherimoya |
| | | | Atemoya |
| | | | Soursop |
| | | | Sweetsop |
| | | | Custard apple |
| | | | Guanabana |
| Piperales | Piperaceae | Piper | Black pepper |
| Poales | Poaceae | Eragrostis | Teff |
| | | Zea | Corn |
| Rosales | Cannabaceae | Cannabis | Hemp |
| Solanales | Convolvulaveae | Ipomea | Sweet potato |
| | Solanaceae | Capsicum | Serrano pepper |
| | | | Thai Chili |
| | | | Piri piri pepper |
| | | Lyceum | Goji/wolf berry |
| | | Solanum | Tomato |
| | | | Potato |
| Zygophyllaceae | Zygophyllales | Tribulus | Goat thorn |
| | | | Puncture vine |

By way of illustration, an extract containing N-trans-caffeoyltyramine is obtained by grinding or pulverizing the dried fruit of *Tribulus terrestris*, subjecting the pulverized material to 80% ethanol at room temperature, filtering and concentrating the 80% ethanol extract, resuspending the concentrated extract in water, partitioning the aqueous solution with hexane, adding chloroform to the aqueous layer, and subjecting the chloroform layer to liquid chromatography with silica gel. See, e.g., Ko, et al. (2015) *Internatl. J. Mol. Med.* 36(4):1042-8.

An extract containing a tyramine containing hydroxycinnamic acid amide can be standardized using conventional techniques such as high-performance liquid chromatography (HPLC) or high-performance thin-layer chromatography (HPTLC) The term "standardized extract" refers to an extract which is standardized by identifying characteristic ingredient(s) or bioactive marker(s) present in the extract. Characterization can be, for example, by analysis of the spectral data such as mass spectrum (MS), infrared (IR), ultraviolet (UV) and nuclear magnetic resonance (NMR) spectroscopic data.

Biological Activity

Biological activity of compounds and/or extracts can be determined using one or more of the well-known biological in vitro assays, in vivo assays and animal models described in more detail below. Each of these assays would provide a measure of the activity of the compounds of the present invention to provide beneficial effects on cellular endpoints linked to metabolic disorders including but not limited to obesity, T2DM, heart disease, stroke, fatty liver disease (NAFLD) and nonalcoholic steatohepatitis (NASH).

Triglyceride Assay in Cultured Hepatocytes.

For measuring triglyceride synthesis in cultured primary hepatocytes, freshly isolated hepatocytes (e.g., from rats) are cultured for 24 hours with normal media (Dulbecco's modified Eagle Medium (DMEM) with 0.25% bovine serum albumin) in the presence or absence of monounsaturated and/or saturated fatty acids (e.g., palmitate (C16:0) or oleate (C18:1), or a 2:1 mixture of the two) and presence or absence of an extract or compound of the invention. Quantitative estimation of hepatic triglyceride accumulation is performed by extraction of hepatic lipids from cell homogenates using chloroform/methanol (2:1) and enzymatic assay of triglyceride mass using an ENZYCHROM™ Triglyceride Assay Kit (Bioassay Systems, Hayward, Calif.).

Adipocyte Glucose Consumption Assay.

Equal amounts ($5 \times 10^5$ cells) of 3T3-L1 pre-adipocytes are seeded and cultured in normal D-glucose, DMEM with 10% fetal bovine serum (FBS), penicillin-streptomycin in a humidified atmosphere of 95% air and 5% $CO_2$ at 37° C. When the cells reach 100% confluence, 3T3-L1 pre-adipocytes are induced to be differentiate by treating the culture with 450 mg/dL D-glucose, 0.32 μM insulin, 0.5 mM 3-isobutyl-1-methylxanthine and 1 μM dexamethasone for 2 days. Subsequently, the culture medium of the differentiated adipocytes is changed to DMEM containing 450 mg/dL D-glucose with or without the administration of a compound or extract of the invention. After 24 hours, the glucose consumption activity is determined by measuring the medium glucose concentration with insulin used as the positive control. Protocols and assays for glucose uptake into cells are available commercially (e.g., ABCAM: Cambridge, Mass.; Promega: Madison, Wis.).

Insulin Secretory Activity.

Insulin-secreting cells, e.g., rat RIN-m5F cells, are plated into 96-well plates and used at subconfluence after a 24-hour incubation. Cells are exposed to 100 μl of sub-toxic concentrations of a compound or extract of the invention and incubated at 37° C. with 5% $CO_2$ for 3 hours. Following treatment, plates are centrifuged at 1000 g for 10 minutes and insulin concentration of supernatants is determined using a solid phase two-site enzyme immunoassay, e.g., DRG Ultrasensitive Rat Insulin ELISA kit (DRG International, Inc.).

Insulin Promoter Activity.

T6PNE cells (Kiselyuk, et al. (2012) *Chem Biol.* 19(7): 806-818; Kiselyuk, et al. (2010) *J. Biomol.* Screen 15(6): 663-70) are seeded at 2000 cells per well in 384-well tissue culture plates in the presence of 1 μM tamoxifen and 0.03 mM palmitate. After a 24-hour incubation, a compound or extract of the invention is added to the cells. Forty-eight hours after compound or extract addition, cells are fixed in 4% paraformaldehyde and stained with DAPI. Blue (DAPI) and green (human insulin promoter driving GFP) channels are imaged.

Triglyceride Assay in Liver.

Mice are provided a compound or extract of the invention. Liver extracts are prepared by homogenization in 0.25% sucrose with 1 mmol/L EDTA, and lipids are extracted using chloroform/methanol (2:1 v/v) and suspended with 5% fatty acid-free bovine serum albumin. Triglyceride levels are measured using triglyceride assay reagents (Sigma Chemical Co.).

Hepatic Triglyceride Secretion In Vivo.

This assay employs the use of TRITON WR1339, which inhibits all lipoprotein lipases and therefore clearance of triglycerides from the blood (Millar et al. 2005. *J. Lipid Res.* 46:2023-2028) Mice are provided a compound or extract of the invention. Subsequently, the mice are injected with 10% TRITON WR1339 per animal by intravenous (IV) injection and blood is collected to assess triglycerides at 0 minutes, 1 hour and 2 hours. Plasma is separated and assayed for triglycerides. Triglyceride secretion rates are expressed as milligram per kilogram per hour after normalizing with their liver weight.

De Novo Lipogenesis Assay.

De novo lipogenesis is thought to be involved in the pathogenesis of NAFLD (Sanders and Griffin. 2016. *Biol. Rev. Camb. Philos. Soc.* 91(2):452-468). Primary hepatocytes from animals treated with a compound or extract of the invention are cultured overnight with 10% DMEM containing insulin (100 nM) and dexamethasone (1 μM). Cells are subsequently incubated with 74 KBq/ml (2-14° C.) sodium acetate (2.07 GBq/mmol) for 1 hour. The cells are lysed with 1 N NaOH, acidified, and lipids are extracted with petroleum ether. Radioactivity is measured by liquid scintillation counter.

Animal Models of T2DM.

Models of T2DM include but are not limited to leptin-deficient mouse (ob/ob; Orel, et al. (2006) Diabetes 55(12): 3335-43; Wang, et al. (2014) *Curr. Diabetes Rev.* 10(2):131-145), the leptin-receptor-deficient mouse (db/db; Wang, et al. (2014) *Curr. Diabetes Rev.* 10(2):131-145), the obese Zucker rat (fa/fa; Shiota & Printz (2012) *Methods Mol. Biol.* 933:103-23), the Wistar Kyoto rat (fa/fa; Figlewicz, et al. (1986) *Peptides* 7:61-65), proopiomelanocortin-deficient mice (POMC$^{-/-}$; Yaswen, et al. (1999) *Nat. Med.* 5:1066-1070), melanocortin 3 and 4 receptor knockout animals (Huszar, et al. (1997) *Cell* 88:131-141; Butler, et al. (2000) *Endocrinology* 141(9):3518-21; Mul, et al. (2011) *Obesity* (Silver Spring) 20(3):612-21; Chen, et al. (2000) *Nat. Genet.* 26(1):97-102), animals overexpressing glucose transporter subtype 4 (Shepard, et al. (1993) *J. Biol. Chem.* 268:22243-22246) and neuron-specific insulin receptor knockout mice (NIRKO mice; Bruning, et al. (2000) *Science* 289:2122-2125). Reviews of the use of such animal models are available (e.g., Chatzigeorgiou et al. 2009. A.J.K. 2012. *Br. J. Pharmacol.* In Vivo 28:345-358; King, 166:877-894). These models are characterized by insulin resistance, hyperglycemia, and hyperinsulinemia, symptoms mirrored in human T2DM. Animals are provided with a compound or extract of the invention and maximum tolerated dose and improvements in metabolism are evaluated.

Animal Model of Lipodystrophy.

The complete lack of fat tissue (lipodystrophy) leads to similar metabolic changes as severe obesity and is associated with insulin resistance. Genetically modified mice with a lack of adipose tissue are characterized by hyperphagia, hepatic steatosis, hypertriglyceridaemia, insulin resistance and T2DM (Savage (2009) *Dis. Model Mech.* 2 (11-12): 554-62). Due to the lack of functional adipose tissue, these mice are leptin deficient and are of use in assessing the effect of the compound or extract of this invention on dysregulated metabolism. Such models are useful for demonstrating in vivo response for compounds of the present invention and exploring key concepts such as dose-response.

Rat Models of Diet-Induced Obesity.

Outbred Sprague-Dawley rats have been used as a polygenic model of obesity (Levin, et al. (1997) *Am. J. Physiol.* 273(2 Pt 2):R725-30). Similarly, rats offered a varied and palatable diet which mimics the so-called Western diet of humans (cafeteria diet) become obese due to hyperphagia (Rogers & Blundell (1984) *Neurosci. Biobehav. Rev.* 8(4): 441-53). Likewise, animals exposed to high-fat (HF) diets develop obesity and exhibit reductions in insulin and leptin sensitivity (Clegg, et al. (2011) *Physiol. Behav.* 103(1):10-6; Hariri & Thibault (2010) *Nutr. Res. Rev.* 23(2):270-99) Such models are useful for demonstrating in vivo response for compounds of the present invention and exploring key concepts such as dose-response.

Mouse Models of Diet-Induced Obesity.

Diet-induced obese (DIO) mice are the standard to study lipotoxicity in vivo (Kennedy, et al. (2010) *Disease Models & Mechanisms* 3(3-4):156-66). High fat fed mice develop abnormalities in both the liver and pancreas. Depending on the genetic background, they develop insulin resistance with or without β-cell atrophy and overt diabetes when on a high-fat diet (Leiter & Reifsnyder (2004) Diabetes 53 Suppl. 1:S4-11; Tschop & Heiman (2001) *Exp. Clin. Endocrinol. Diabetes* 109(6):307-19). Strains of mice that differ in propensity to develop β-cell atrophy include, e.g., NONcN-ZO10/LtJ (The Jackson Laboratory, Bar Harbor, Me.) that develops β-cell atrophy and C57BL/6J (The Jackson Laboratory, Bar Harbor, Me.) that does not exhibit β-cell loss. Using these models, the effect of normal vs. high fat diet±test compound can be analyzed. Approximately half of NONcNZ0l10/LtJ males become diabetic and often develop islet atrophy on a high fat diet (Leiter (2009) *Methods Mol. Biol.* 560:1-17). Other strains that may be studied include the DIO mouse on the C57B1/6 background which is not highly prone to β-cell loss but is a good model of pre-T2D and obesity with elevated blood glucose and impaired glucose tolerance (Leiter (2009) *Methods Mol. Biol.* 560:1-17). C57B1/6KsJ db/db mice develop diabetes associated with β-cell failure (Hummel, et al. (1972) *Biochem. Genet.* 7(1): 1-13), which has been shown to be correctable by MafA overexpression (Matsuoka, et al. (2015) *J. Biol. Chem.* 290:7647-7657), suggesting their use in an efficacy trial. Such models are useful for demonstrating in vivo response for compounds of the present invention and exploring key concepts such as dose-response.

Animal Model of Metabolic Syndrome. New Zealand obese (NZO) mouse are obese and have severe T2DM. A number of genetic susceptibility loci that favor the development of adiposity and hyperglycemia have been identified in NZO mice. In addition to the leptin receptor gene, several genes of transcription factors were identified as potential candidate genes and orthologs of some of these genes have been linked to the human metabolic syndrome (Joost (2010) *Results Probl. Cell Differ.* 52( ):1-11). Such models are useful for demonstrating in vivo response for compounds of the present invention and exploring key concepts such as dose-response.

Counter Screens.

Counter screens are often used to select among a library of compounds in order to avoid off target effects. In the present invention, the activity of compounds as modulators of HFN4α activity is the desired target even though other off target effects may occur. Drugs that have been marketed for use in humans based on target effects other than HFN4α have subsequently been shown to have activity as HNF4α activators (Alverine and Benfluorex; Lee, et al. (2013) *ACS Chem. Biol.* 8(8):1730-6). Alverine has been marketed as a smooth muscle relaxant for gastrointestinal disorders, while Benfluorex was marketed as an anorectic agent. Benfluorex was known to be metabolized by cleavage of an ester moiety into fenfluramine, a potent agonist of serotonin 5-hydroxytryptamine 2(5-$HT_2$) receptors, an effect that was thought to be related to its activity as an anorectic agent (Porter, et al. (1999) *Br. J. Pharmacol.* 128(1):13-20). However, modulation of 5-$HT_2$ receptors by Benfluorex was linked to undesirable cardiopulmonary side effects. Accordingly, based on these experiences with synthetic compounds, compounds and extracts of the present invention will be tested for off target effects on 5-hydroxytryptamine receptor activation using, e.g. a fluorometric imaging plate reader (FLIPR) assay, which allows rapid detection of rises in intracellular calcium levels in cells expressing a human 5-$HT2_A$, 5-$HT_{2B}$ or 5-$HT_{2C}$ receptor in CHO-K1 cells. See, e.g., Porter, et al. (1999) *Br. J. Pharmacol.* 128(1):13-20. Other counter screens may be chosen based on initial studies where toxic effects may be linked to other off target actions.

Formulations

A substantially pure compound or extract comprising a compound of this invention can be combined with a carrier and provided in any suitable form for consumption by or administration to a subject. In this respect, the compound or extract is added as an exogenous ingredient or additive to the consumable. Suitable consumable forms include, but are not limited to, a dietary supplement, food ingredient or additive, a medical food, nutraceutical or pharmaceutical composition.

A food ingredient or additive is an edible substance intended to result, directly or indirectly, in its becoming a component or otherwise affecting the characteristic of any food (including any substance intended for use in producing, manufacturing, packing, processing, preparing, treating, packaging, transporting, or holding food). A food product, in particular a functional food, is a food fortified or enriched during processing to include additional complementary nutrients and/or beneficial ingredients. A food product according to this invention can, e.g., be in the form of butter, margarine, sweet or savory spreads, condiment, biscuits, health bar, bread, cake, cereal, candy, confectionery, soup, milk, yogurt or a fermented milk product, cheese, juice-based and vegetable-based beverages, fermented beverages, shakes, flavored waters, tea, oil, or any other suitable food.

A dietary supplement is a product taken by mouth that contains a compound or extract of the invention and is intended to supplement the diet. A nutraceutical is a product derived from a food source that provides extra health benefits, in addition to the basic nutritional value found in the food. A pharmaceutical composition is defined as any component of a drug product intended to furnish pharmacological activity or other direct effect in the diagnosis, cure, mitigation, treatment, or prevention of disease, or to affect the structure or any function of the body of humans or other animals. Dietary supplements, nutraceuticals and pharmaceutical compositions can be found in many forms such as tablets, coated tablets, pills, capsules, pellets, granules, softgels, gelcaps, liquids, powders, emulsions, suspensions, elixirs, syrup, and any other form suitable for use.

The term "carrier" as used herein means a material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each. carrier should be compatible with the other ingredients of the formulation and not injurious to the subject. Some examples of materials that can serve as carriers include: (1) sugars, such as lactose, glucose and sucrose; (2) starches, such as corn starch and potato starch; (3) cellulose, and its derivatives, such as sodium carboxymethyl cellulose, ethyl cellulose, cellulose acetate, and hydroxyl propyl methyl cellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other nontoxic compatible substances employed in conventional formulations.

For preparing solid compositions such as tablets or capsules, the compound or extract is mixed with a carrier (e.g., conventional tableting ingredients such as corn starch, lactose, sucrose, sorbitol, talc, stearic acid, magnesium stearate, dicalcium phosphate or gums) and other diluents (e.g., water) to form a solid composition. This solid composition is then subdivided into unit dosage forms containing an effective amount of the compound of the present invention. The tablets or pills containing the compound or extract can be coated or otherwise compounded to provide a dosage form affording the advantage of prolonged action.

In particular embodiments of this invention, a consumable composition includes the compound or extract, a carrier and a preservative to reduce or retard microbial growth. The preservative is added in amounts up to about 5%, preferably from about 0.01% to 1% by weight of the film. Preferred preservatives include sodium benzoate, methyl parabens, propyl parabens, sodium nitrite, sulphur dioxide, sodium sorbate and potassium sorbate. Other suitable preservatives include, but are not limited to, salts of edetate, (also known as salts of ethylenediaminetetraacetic acid, or EDTA, such a disodium EDTA).

The liquid forms in which the compound or extract of the invention is incorporated for oral or parenteral administration include aqueous solution, suitably flavored syrups, aqueous or oil suspensions, and flavored emulsions with edible oils as well as elixirs and similar vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin. Liquid preparations for oral administration may take the form of, for example, solutions, syrups or suspensions, or they may be presented as a dry product for reconstitution with water or other suitable vehicles before use. Such liquid preparations may be prepared by conventional means with acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

Methods of preparing formulations or compositions of this invention include the step of bringing into association a compound or extract of the present invention with the carrier and, optionally, one or more accessory and/or active ingredients. In general, the formulations are prepared by uniformly and intimately bringing into association a compound or extract of the present invention with liquid carriers, or finely divided solid carriers, or both, and then, if necessary, shaping the product. As such, the disclosed formulation may consist of, or consist essentially of a compound or extract described herein in combination with a suitable carrier.

When a compound or extract of the present invention is administered as pharmaceuticals, nutraceuticals, or dietary supplements to humans and animals, they can be given per se or as a composition containing, for example, 0.1 to 99% (more preferably, 10 to 30%) of active ingredient in combination with an acceptable carrier.

A consumable product may be consumed by a subject to provide less than 100 mg of a compound disclosed herein per day. In certain embodiments, the consumable provides between 10 and 60 mg/day of a tyramine containing hydroxycinnamic acid amide. The effective amount can be established by methods known in the art studies and be dependent upon bioavailability, toxicity, etc.

While it is contemplated that individual tyramine containing hydroxycinnamic acid amides may be used in the consumables of this invention, it is further contemplated that two or more of the compounds or extracts could be combined in any relative amounts to produce custom combinations of ingredients containing two or more tyramine containing hydroxycinnamic acid amides in desired ratios to enhance product efficacy, improve organoleptic properties or some other measure of quality important to the ultimate use of the product.

Molecular Target

HNF4α (hepatocyte nuclear factor 4α) is a global nuclear transcription factor, regulating expression of many genes involved in maintaining balanced metabolism (homeostasis). Notably, HNF4α is expressed in both the liver (hepatocytes) and pancreas (β-cells). The expression and transcriptional activity of HNF4α is decreased in NAFLD and T2DM in both human liver cells and human pancreatic β-cells. HNF4α is mutated in MODY1, an autosomal dominant monogenic form of diabetes, providing human genetic evidence for a direct role in diabetes pathogenesis. HNF4α gene expression is down-regulated in T2D. In addition, free fatty acids, which are elevated in overweight and obese individuals, inhibit HNF4α activity. In view of the fact that HNF4α haplo insufficiency causes diabetes and HNF4α is down-regulated in T2D, restoration of or an increase in HNF4α activity to the normal wild-type state would provide an overall health and therapeutic benefit.

HNF4α-knockout rodent models exhibit the fatty liver phenotype, as well as reduced lipogenesis, reduced de-novo cholesterol synthesis, reduced very-low-density lipoprotein (VLDL) secretion and high-density lipoprotein (HDL) biogenesis, as well as increased insulin intolerance. In addition, knockout mice show enhanced uptake of FFAs and reduced degradation via β-oxidation. This results in hypocholesterolemia, low blood triglyceride levels, and hepatic steatosis. All of this represents a significant dysregulation of lipid metabolism resulting from HNF4α deficiency (Yin, et al. (2011) *Arterioscler. Thromb. Vasc. Biol.* 31(2):328-336; Hayhurst, et al. (2001) *Mol. Cell Biol.* 21(4)1393-1403; Martinez-Jimenez (2010) *Mol. Cell. Biol.* 30(3):565-577). By comparison, increased expression of HNF4α in the liver may increase transcription of genes that promote hepatic FFA oxidation, ketogenesis, and very-low density lipoprotein (VLDL) secretion, as a means to deal with excess FFA accumulation (Martinez-Jimenez (2010) *Mol. Cell. Biol.* 30(3):565-577). Therefore, HNF4α provides a target for mitigating the adverse effects of FFAs, which are characteristically elevated in NAFLD.

In T2DM, HNF4α is responsible for direct regulation of genes involved in glucose transport and glycolysis. Without HNF4α in β-cells, rodents exhibit defective glucose-stimulated insulin secretion in (β-cells—meaning decreased insulin secretion (Gupta, et al. (2005) *J. Clin. Invest.* 115(4) 1006-15). It has been observed that HNF4α gene expression is downregulated in individuals with T2DM, likely due to exposure to chronically elevated FFAs. In particular, it has been shown that free palmitic acid (a C16 saturated FA) impairs pancreatic β-cell function and viability and suppresses normal insulin production due to actions on HNF4α (Lee, et al. (2013) *ACS Chem. Biol.* 8(8):1730-1736). Therefore, HNF4α provides a target for ameliorating the symptoms of T2DM.

Metabolic Disorders

The term "metabolic disorder" refers to a disorder or condition that occurs when the body is unable to properly metabolize carbohydrates, lipids, proteins, and/or nucleic acids. Accordingly, in the context of the present invention disorders relating to abnormality of metabolism are encompassed in the term "metabolic disorder." The term metabolic disorder includes, but is not limited to, insulin resistance, hyperglycemia, diabetes mellitus (in particular T2DM), obesity, glucose intolerance, hypercholesterolemia, hyperlipoproteinemia, dyslipidemia, hyperinsulinemia, atherosclerotic disease, coronary artery disease, metabolic syndrome, hypertension, or a related disorder associated with abnormal plasma lipoprotein, triglycerides or a disorder related to glucose levels such as pancreatic beta cell regeneration.

T2DM refers to a chronic disease or condition, which occurs when the pancreas does not produce enough insulin, or when the body cannot effectively use the insulin it produces. This leads to an increased concentration of glucose in the blood (hyperglycemia). Based on studies that have established a relationship between plasma glucose concentrations, measures of glycemic exposure, and risk of diabetic retinopathy, the following criteria have been adopted for the diagnosis of diabetes mellitus: fasting plasma glucose greater than or equal to 126 mg/dL (7.0 mmol/L); plasma glucose greater than or equal to 200 mg/dL (11.1 mmol/L) at 2 hours following ingestion of 75 g anhydrous glucose in an oral glucose tolerance test; or random plasma glucose greater than 200 mg/dL (11.1 mmol/L) in a person with symptoms of diabetes. Other important definitions include: impaired glucose tolerance with a plasma glucose equal to or greater than 140 mg/dL (7.8 mmol/L) but less than 200 mg/dL (11.1 mmol/L) at 2 hours in the oral glucose tolerance test; and impaired fasting glucose with a fasting plasma glucose (FPG) equal to or greater than 100 mg/dL (5.6 mmol/L) but less than 126 mg/dL. A compound or extract of the invention is said to modulate metabolism by decreasing one or more of fasting plasma glucose, plasma glucose following ingestion of 75 g anhydrous glucose, or random plasma glucose levels below those referenced herein. Another endpoint that can be monitored as part of assessment of metabolic activity is blood levels of HbA1c; HbA1c is a measure of average glucose levels in blood over the past two to three months. Levels of HbA1c are used as clinical indicators of risk of diabetes, where increased levels are indicative of an increased risk of T2DM. Thus, reduction in HbA1c can also be used to support an indication of glycemic control.

Obesity is a chronic, relapsing health risk defined by excess body fat. Total body fat can be accurately measured using hydrodensitometry and dual-energy x-ray absorptiometry (DEXA). Because body mass index (BMI), expressed as kilograms of weight divided by height in meters squared is simple and inexpensive to calculate, and correlates strongly with total body fat in non-elderly adults, it is commonly used as a surrogate for total body fat. Obesity is defined by the National Institutes of Health as having a BMI of 30 kg/m$^2$ or higher. The relationships between BMI and risks for death and major comorbidities vary by age, sex, race, and smoking status, but, in general, are lowest in individuals with BMIs of 18.5 kg/m$^2$ to 24.9 kg/m$^2$ and increase in a curvilinear or linear manner with BMIs of 25 kg/m$^2$ to approximately 40 kg/m$^2$. A compound or extract of the invention is said to modulate metabolism by decreasing mean and/or categorical body weight. Mean body weight is defined as the difference in mean percent loss of baseline body weight in the active product-treated versus placebo-treated group. Categorical body weight is defined as the proportion of subjects who lose at least 5 percent of baseline body weight in the active product-treated versus placebo-treated group. Secondary efficacy endpoints can include, but are not limited to, improvements in blood pressure and pulse, lipoprotein lipids, fasting glucose and insulin, HbA1c (in T2DM), waist circumference, and quality of life.

NAFLD, or "fatty liver," is a metabolic disease characterized by excessive accumulation of fat in the liver. NAFLD is characterized by predominantly macrovesicular steatosis and the presence of visible steatosis in >5% of hepatocytes is generally accepted as a working definition of a fatty liver (Kleiner, et al. (2005) *Hepatology* 41:1313-1321) Nonalcoholic steatohepatitis or NASH is the most extreme form of NAFLD and is considered as a major cause of cirrhosis of liver of unknown etiology. The minimal criteria for the diagnosis of NASH include the presence of liver cell >5% macrovesicular steatosis, inflammation and ballooning, typically with a predominantly centrilobular (acinar zone 3) distribution in adults. Steatohepatitis is not simply the presence of inflammation and steatosis but is a specific histologic entity (Kleiner, et al. (2005) Hepatology 41(6):1313-21; Brunt, et al. (1999) *Am. J. Gastroenterol.* 94:2467-2474; Ludwig, et al. (1980) *Mayo Clin. Proc.* 55:434-438; Neuschwander-Tetri & Caldwell (2003) *Hepatology* 37:1202-1219). A compound or extract of the invention is said to modulate metabolism by measurably reducing the accumulation of fat in the liver thereby improving liver function.

The term metabolic syndrome represents a cluster of laboratory and clinical findings that serve as markers for increased risk for coronary heart disease, stroke, peripheral vascular disease and/or T2DM. Risk factors associated with metabolic syndrome include abdominal obesity (i.e., excessive fat tissue in and around the abdomen), atherogenic dyslipidemia including but not limited to high triglycerides, low HDL cholesterol and high LDL cholesterol, elevated blood pressure, insulin resistance or glucose intolerance, prothrombotic state (e.g., high fibrinogen or plasminogen activator inhibitor-1 in the blood), and/or proinflammatory state (e.g., elevated C-reactive protein in the blood). A compound or extract of the invention is said to modulate metabolism by improving components of metabolic syndrome and ultimately shown to prevent the development T2DM and reduce cardiovascular morbidity and mortality.

Metabolism Modulation

This invention also provides methods for modulating metabolism to ameliorate, prevent or treat a metabolic disorder. In accordance with such methods, an effective amount of a compound or extract of this invention is administered to a subject in need of treatment so that the subject's metabolism is modulated thereby addressing the underlying pathogenesis of one or more metabolic disorders and promoting the health, well-being, and quality of life of the subject. The term "subject" as used herein refers to an animal, preferably a mammal. In some embodiments, the subject is a veterinary, companion, farm, laboratory or zoological animal. In other embodiments, the subject is a human.

A subject in need of treatment includes a subject with observable symptoms of a metabolic disorder (e.g., a subject with abnormal glucose or lipid metabolism), as well as a subject who has no disorder but has been observable symptoms of a metabolic determined to be susceptible to developing the metabolic disorder (i.e., a subject at risk of developing the metabolic disorder). For example, according to the American Heart Association, metabolic syndrome (which raises the risk of heart disease, diabetes, stroke, and other health problems) is diagnosed when any three of the following five risk factors are present: high blood glucose (sugar); low levels of HDL ("good") cholesterol in the blood; high levels of triglycerides in the blood; large waist circumference or "apple-shaped" body; or high blood pressure.

By way of further illustration, autoantibodies to insulin (IAA); glutamic acid decarboxylase (GAD); and an islet cell member of the receptor type of the tyrosine phosphate family termed IA-2 have been identified as markers that predate the clinical onset of T2DM. See, e.g., U.S. Pat. Nos. 6,391,651 and 6,316,209. Similarly, C-reactive protein (CRP), apolipoprotein CIII, and plasma homocysteine levels have been identified as markers for identifying subjects at risk for high cholesterol (or hypercholesterolemia or hyperlipidemia) See, e.g., US 2004/0198656; Yeh (2004) Can. J. Cardiol. 20(Suppl B):93-96B; and Geisel, et al. (2003) Clin. Chem. Lab. Med. 41(11):1513-7. Additional factors that can be used, alone or in combination, to determine whether a subject is at risk or predisposed to developing hypercholesterolemia include, without limitation, heredity (i.e., familial hypercholesterolemia), high blood pressure, history of smoking, alcohol consumption, diabetes, obesity, physical inactivity, age and sex (i.e., post-menopausal women over the age of 50), and stress.

The term "effective amount" as used herein means an amount of the compound, extract, or formulation containing the compound or extract, which is sufficient to significantly improve a disorder. Of concern when determining an effective amount to be used in humans is balancing the desired effects (benefits) against risks associated with use of a compound. At issue for such risk/benefit assessments is the types of adverse effects observed and the likelihood that they will occur. Also considered is the fact that the effective amount may vary with the particular disorder being treated, e.g., diabetes mellitus or obesity, the age and physical condition of the end user, the severity of the condition, the duration of the treatment, the particular carrier utilized, and like factors.

In general, a suitable daily dose of a compound or extract of the invention will be that amount of a compound or extract which is the lowest dose that is effective at producing a desired benefit, in this case an effect that improves metabolism of fats and sugars and consequently supports overall health and well-being. Such an effective dose will generally depend upon the factors described herein. For oral administration, the dose may range from about 0.0001 mg to about 10 grams per kilogram of body weight per day, about 5 mg to about 5 grams per kilogram of body weight per day, about 10 to about 2 grams per kilogram of body weight per day, or any other suitable dose. If desired, the effective daily dose of the compound or extract may be administered as two, three, four, five, six or more sub-doses administered separately at appropriate intervals throughout the day, optionally, in unit dosage forms. Preferred dosing is one administration per day.

The compound or extract of the invention can be used alone or in combination with a particular diet (e.g., foods with a low glycemic index) or standard of care.

Administration of a compound or extract of the invention modulates the metabolism of a subject thereby addressing the underlying pathogenesis of one or more metabolic disorders and/or promoting the health, wellbeing, and quality of life of the subject. Ideally, an effective amount of a compound or extract provides a measurable improvement in the levels or activity of one or more metabolic compounds. Examples include HNF4α activity, insulin-like growth factor levels (such as insulin-like growth factor 1 or IGF-1), blood sugar levels, insulin levels, C peptide levels, triglyceride levels, free fatty acid levels, blood uric acid levels, microalbuminuria levels, glucose transporter expression, adiponectin levels, total serum cholesterol levels, high density lipoprotein (HDL) levels, and/or low density lipoprotein (LDL) levels.

More particularly, administration of a compound or extract of the invention improves metabolism, liver function, fasting plasma glucose levels, postprandial plasma glucose levels, glycosylated hemoglobin HbA1c, body weight, insulin sensitivity, serum lipid profile by improving lipid clearance, or a combination thereof. In particular embodiments, use of a compound or extract of the invention preferably prevents, slows the progression of, delays or treats a metabolic disorder such as T2DM, impaired glucose tolerance, impaired fasting blood glucose, hyperglycemia, postprandial hyperglycemia, hyperinsulinemia, NASH, NAFLD, or metabolic syndrome; slows the progression of, delays or treats pre-diabetes; improves glycemic control and/or reduces fasting plasma glucose, postprandial plasma glucose and/or glycosylated hemoglobin HbA1c; prevents, slows, delays or reverses progression of impaired glucose tolerance, impaired fasting blood glucose, insulin resistance or metabolic syndrome to T2DM; prevents, slows the progression of, delays, prevents or treats a complication of diabetes mellitus such as cataracts or a micro- or macrovascular disease, such as nephropathy, retinopathy, neuropathy, tissue ischemia, diabetic foot, dyslipidemia, arteriosclerosis, myocardial infarction, acute coronary syndrome, unstable angina pectoris, stable angina pectoris, stroke, peripheral arterial occlusive disease, cardiomyopathy, heart failure, heart rhythm disorders or vascular restenosis; reduces body weight and/or body fat, or prevents an increase in body weight and/or body fat, or facilitates a reduction in body weight and/or body fat; prevents, slows, delays or treats diseases or conditions attributed to an abnormal accumulation of ectopic fat, in particular liver fat; maintains and/or improves insulin sensitivity and/or treats or prevents hyperinsulinemia and/or insulin resistance; reduces fat deposits; prevents, slows, delays or reverses progression of fatty liver to NASH; and/or prevents, slows, delays or reverses progression of NASH to cirrhosis, end-stage liver disease and/or hepatocellular carcinoma.

The following non-limiting examples are provided to further illustrate the present invention.

Example 1: Assessing Indicators of Metabolic Activity: Materials and Methods

Expression of Insulin and HNF4α.

RNA was purified using a RNEASY® chromatographic separation and isolation kits (Qiagen), and converted to cDNA using the gScript™ cDNA SuperMix (Quanta Biosciences). Q-PCR was conducted with cDNA corresponding to 2 μg of RNA using an Opticon Real-Time System (MJ Research) and QPCR SuperMix (BioPioneer). See All mRNA values were normalized to 18S rRNA values and are expressed as fold changes over vehicle-treated control.

Counter-Screen for Estrogenic Activity.

Estrogenic activity was monitored by co-transfection of a reporter plasmid containing a multimerized E-box 5' of a minimal promoter fused to the Firefly luciferase gene (4RTK-luc) with wild-type E47 or E47MER (Kiselyuk, et al. (2010) *J. Biomol.* Screen 15(6):663-70). HeLa cells were transfected using polyethylenimine, 0.2 μg 4RTK-Luc plasmid and either 0.3 μg of human E47, E47MER or pMSCVhph vector in 50 μl of serum-free Dulbecco's modification of Eagle medium per well. Transfections included *Renilla luciferase* (pRL-TK) plasmid as a control for transfection efficacy. Transfection conditions were as described in the PPRE-Luc reporter assay of Kiselyuk, et al. ((2010) *J. Biomol.* Screen 15(6):663-70). Sixteen hours after transfection, culture media were changed and maintained for 48 hours with tamoxifen and/or compound or vehicle (DMSO). Cells were then lysed and assayed for luciferase activity using the Promega DUAL-LUCIFERASE® reporter assay kit (Promega Corp., Madison, Wis.), and luminescence was measured using the Veritas™ Microplate Luminometer (Turner Biosystems, Sunnyvale, Calif.). Data were normalized to *Renilla luciferase* (pRL-TK) and expressed as fold-change over vehicle alone.

Inhibition of HNF4α GFP Expression. Using the insulin promoter assay described herein, activity of HNF4α was assessed in the presence of BI-6015 (0, 2.5, 5 μM), a known antagonist of HNF4α (Kiselyuk, et al. (2012) *Chem. Biol.* 19(7):806-818), in combination with N-trans-caffeoyltyramine (0, 5, 10, 20 μM).

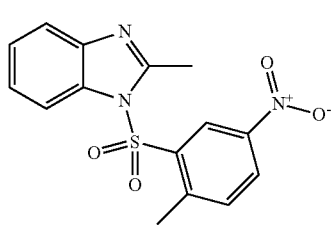

BI-6015

Hepatic Microsome Assay.

Hepatic microsomes stability assays were performed in accordance with known methods (Peddibhotla, et al. (2013) *ACS Med. Chem.* Lett. 4:846-851). Briefly, 3 μL of 25 μM compound solution in acetonitrile were incubated with 123 μL of mouse, human or rat liver microsomes (Xenotech, Kansas City, Kans.). After preincubation at 37° C. for 10 minutes, enzyme reactions were initiated by adding 120 μL of NADPH-generating system (2 mM NADP$^+$, 10 mM glucose-6-phosphate, 0.4 U/ml glucose-6-phosphate dehydrogenase, and 5 mM MgCl$_2$) in the presence of 100 mM potassium phosphate buffer (pH 7.4) The final concentration of each compound used was 1 μM. The microsomal concentrations used were 1.0 mg/mL. Compounds were incubated in microsomes for 0, 5, 15, 30 and 60 minutes. The reactions were stopped by the addition of ice cold ACN and the reaction mixtures were centrifuged at 10,000 g for 10 minutes before the supernatant was removed for analysis. A 10 μL portion of the resulting extract was injected on a Thermo HPLC system equipped with PAL CTC plate sampler (96-well plate), Dionex Ultimate 3000 binary pump (flow rate at 0.600 mL/min), Dionex Ultimate 3000 thermostatted column compartment (temperature at 40° C.), Thermo Endura Mass Spectrometer (ESI source), using a Thermo Scientific Accucore C18 (2.6 μM, 2.1×50 mm) column. A gradient was run starting at 95% H$_2$O (0.1% formic acid) and 5% ACN (0.1% formic acid) during the first 0.5 min, then under gradient condition of 5-100% ACN (0.1% formic acid) from minute 0.5 to 3.5, finishing at 95% H$_2$O (0.1% formic acid) and 5% ACN (0.1% formic acid) over 0.5 min, with another 1 min at 95:5 to re-equilibrate.

Lipid Clearance in HepG2 and T6PNE Cells (Steatosis Assay).

The steatosis assay was carried out as described (Kiselyuk, et al. (2012) *Chem. Biol.* 19(7):806-818) with the exception of the drug concentration, which was 20 μM for N-trans-caffeoyltyramine with 0.25 mM palmitate in HepG2 cell lines, and 10 μM of either N-trans-caffeoyltyramine, N-trans-caffeoyltyramine, or pcoumaroyltyramine, with 0.25 mM palmitate in T6PNE cell lines. Steatosis was assessed using the Oil Red O Method for Fats kits (Poly Scientific; Warrington, Pa.), per manufacturer's guidelines. Briefly, frozen tissue slides or fixed cells were incubated in neat propylene glycol for 2 minutes and Oil Red O solution for 15 hours for slides or 1 hour for fixed cells, differentiated in 85% propylene glycol solution for 1 minute, washed twice with distilled water and stained in Hematoxylin of 10 seconds. Slides were mounted with glycerin jelly mounting medium.

Alkaline Phosphatase (ALP) Quantitation.

Increased levels of ALP in blood are considered indicative of liver function abnormalities. Thus, ALP was assayed in accordance with known methods (Kiselyuk, et al. (2012) *Chem. Biol.* 19(7):806-818). Briefly, prior to sacrifice, blood was drawn and analyzed using a Vet Scan blood analyzer, measuring alkaline phosphatase (ALP, IU/L), alanine aminotransferase (ALT, IU/L), gamma glutamyl transferase (GGT, IU/L), bile acids (BA, μmol/L), total bilirubin (TBIL, mg/dL), albumin (ALB, g/dL), blood urea nitrogen (BUN, mg/dL), and cholesterol (CHOL, mg/dL).

Triglyceride (TG) Quantitation.

TG quantity was assayed using a Triglyceride Colorimetric Assay Kit (Cayman Chemicals; Ann Arbor, Mich.) according to the manufacturer's instructions.

Lipid Droplet Size Analysis.

All slides were scanned at a magnification of 20× using the Aperio Scanscope FL system (Aperio Technologies Inc.; Vista, Calif.). The appropriate dyes were assigned and illumination levels were calibrated using a preset procedure; the parameters were saved and applied to all slides. The acquired digital images represented whole tissue sections. Sections were evaluated for image quality. All acquired images were subsequently placed in dedicated project folders, and stored on a designated local server. Selected areas of the slides were selected using Aperio Imagescope (version 12 Aperio Technologies Inc.). For analysis, slides were viewed, whole tissue areas were selected and analyzed using the web-based Image Scope viewer. Slides were quantified using the 'Color Deconvolution v9' algorithm for oil redo staining (version 11 Aperio Technologies Inc.). The algorithm was optimized using a preset procedure to maximize the strong red color positive oil droplets signal to noise ratio and the subsequent macro was saved and applied to all slides.

HNF4α Immunostaining in Organ Samples.

Samples were harvested from mice, fixed in 4% paraformaldehyde and embedded in paraffin or O.C.T. freezing media (Sakura Finetek; Torrance, Calif.) Slides of 5 μm thickness were washed four times with PBS and treated with 0.3% Triton™ in PBS for 10 minutes. Antigen retrieval was carried out with CitriSolv™ (Fisher Scientific; Waltham, Mass.) for 10 minutes in sub-boiling temperature. After washing with PBS for 10 minutes, slides were incubated in blocking solution with 5% normal donkey serum (Jackson Immuno Research; West Grove, Pa.) for 60 minutes at room temperature. Cells were fixed in 4% paraformaldehyde for 15 minutes on 4° C. and washed with PBS, treated with 0.3% Tri Ton™ in PBS for 10 minutes and blocked as previously described for slide samples.

Primary Antibodies.

HNF4α antibodies were used (#sc-6556, Santa Cruz Biotechnology; Santa Cruz, Calif. and #3113, Cell Signaling Technology; Danvers, Mass.). For fluorescent imaging, samples were incubated with ALEXA FLOUR® 488 green-fluorescent dye or Rhodamine labeled anti-mouse, rabbit or goat and nuclei were counterstained with DAPI (4',6-diamidino-2-phenylindole) Controls using secondary antibodies alone were used to ensure specificity of immunostaining. Fluorescently labeled sections were analyzed with a conventional inverted microscope (Olympus, PlanFl 40x/0.60) or with a confocal microscope equipped with a krypton/argon laser.

Bioavailability Determinations.

Male C57BL/6 mice were administered N-trans-caffeoyltyramine or N-trans-feruloyltyramine via IV, intraperitoneal or oral route (three mice for each route) (Table 2).

TABLE 2

| Route | Formulation | Dosage (mg/kg) |
| --- | --- | --- |
| IV | 1 mg/mL in 75% PEG 300/25% water, clear solution | 2.0 |
| Oral | 3 mg/mL in 0.5% methyl cellulose, homogenous opaque suspension with fine particles | 30.0 |
| IP | 3 mg/mL in 5% DMSO/5% Polysorbate 89/90% water, clear solution | 30 |

A blood sample from each mouse was drawn at 0.25, 0.5, 1, 2, 4, 6 and 24 hours after administration. An 8 μL aliquot of blood was used for analysis. After adding 200 μL of an internal standard comprising 100 ng/mL Labetalol, 100 ng/mL dexamethasone, 100 ng/mL tolbutamide, 100 ng/mL Verapamil, 100 ng/mL Glyburide, and 100 ng/mL Celecoxib in ACN, the mixture was vortex-mixed and centrifuged at 12000 rpm for 15 minutes at 4 QC to pellet precipitated protein. Four μL of the supernatant was injected for LC-MS/MS analysis. Bioavailability (%) was calculated using $AUC_{0-inf}$ (% $AUC_{Extra}$<20%) or $AUC_{0-last}$ (% $AUC_{Extra}$>20%) with nominal dose.

pH Stability Assessment.

Individual stock solutions were prepared in DMSO at concentrations of 10 mg/mL. Four different buffer solutions were prepared to achieve solutions with a pH of 2, 7.4, 8.5 and 10. For each pH assay, 5 μL of stock solution was added to 245 μL of buffered solution to a 2 mL tube, vortexed and incubated in a 37° C. water bath. At each timepoint, 50 μL aliquots were taken, neutralized and analyzed via HPLC analysis using a DAD detector at 280 nm. The fold change of the peak area at 280 nm was analyzed for the initial and final timepoint, 0.5 and 72 hours, respectively.

Example 2: Assessing Compounds for Activity as HNF4α Agonists

Given the role of HNF4α in maintaining a healthy metabolism in humans, test compounds were screened for activity as HNF4α agonists (either direct or indirect effects). Using a known insulin promoter-reporter assay, Kiselyuk and colleagues (2010. J. Biomol. Screen 15(6):663-70), screened a library of compounds for activity to promote insulin activation. They identified compound 1 as an insulin activator (Kiselyuk, et al. (2012) Chem. Biol. 19(7):806-18) and the compound was subsequently shown to possess HNF4α agonistic activity in an ornithine transcarbamoylase (OTC) promoter assay. The OTC promoter is known to be responsive to HNF4α in transient transfection assays (Inoue, et al. (2002) J. Biol. Chem. 277:25257-65).

To identify plant compounds that have similar bioactivity as this synthetic agent (compound 1), a bioinformatics approach was taken to predict, from the set of all known plant compounds, a targeted sub-set with the desired HNF4α agonistic activity. Using a number of algorithms in combination with training data (i.e., positive data), models were built around important features of the positive data, which were predictive of the desired biological activity. More specifically, a set of 18 synthetic compounds with known ability to affect HNF4α activity (e.g., compound 1) were included in the positive data set. These structures were used to search a database of plant compounds for chemical structures that had similar structural features. A number of metrics were used to measure similarity based on concepts from the fields of graph theory and information theory, either solely or in combination.

Plant compounds in the top 10th percentile of similarity to the 18 target structures were selected and compounds predicted to be potential agonists of HNF4α activity given their chemical structural features were screened in the HNF4α assay. The results of the screening identified a class of plant tyramine containing hydroxycinnamic acid amides (i.e., N-trans-caffeoyltyramine, N-cis-caffeoyltyramine, N-trans-feruloyltyramine and p-coumaroyltyramine) that are able to act as HNF4α modulators. Notably, N-trans-caffeoyltyramine was determined to be roughly an order-of-magnitude more potent than Alverine in activating HNF4α (FIG. 1) Due to hydroxyl derivatization of both phenyl rings, N-trans-caffeoyltyramine is less lipophilic and therefore expected to be more bioavailable. Overall, the increased potency and expected enhanced bioavailability indicated that N-trans-caffeotyramine and other tyramine containing hydroxycinnamic acid amides would be expected to be more desirable compounds for use in the methods disclosed herein.

Figure 2:
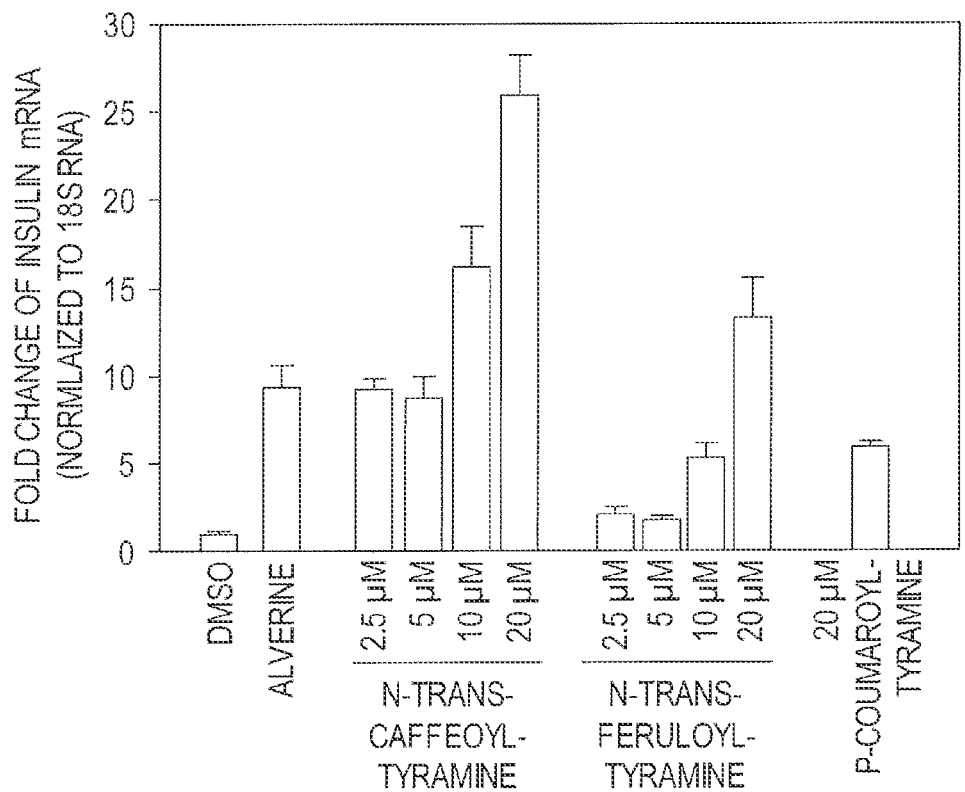
FIG. 2 shows the effect of N-trans-caffeoyltyramine, N-trans-feruloyltyramine and p-coumaroyltyramine on insulin mRNA levels as determined by quantitative PCR. DMSO and alverine (20 μM) were used as negative and positive controls, respectively.
Figure 3:
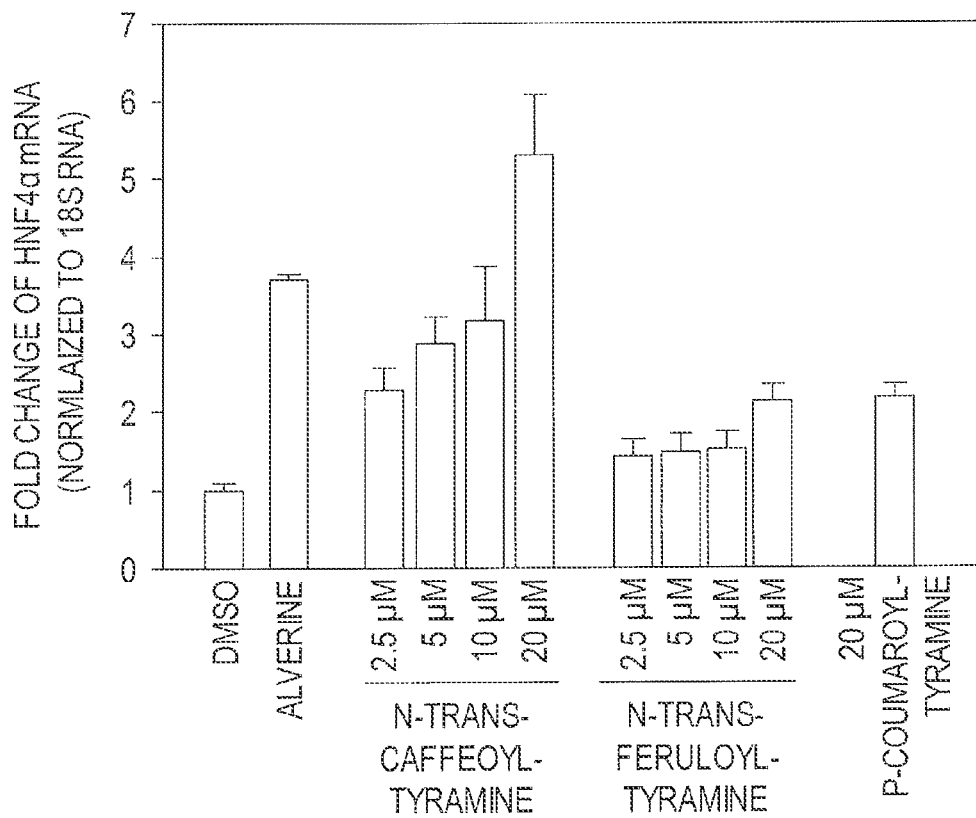
FIG. 3 shows the effect of N-trans-caffeoyltyramine, N-trans-feruloyltyramine and p-coumaroyltyramine on HNF4α mRNA levels as determined by quantitative PCR. DMSO and alverine (20 μM) were used as negative and positive controls, respectively.
Figure 4:
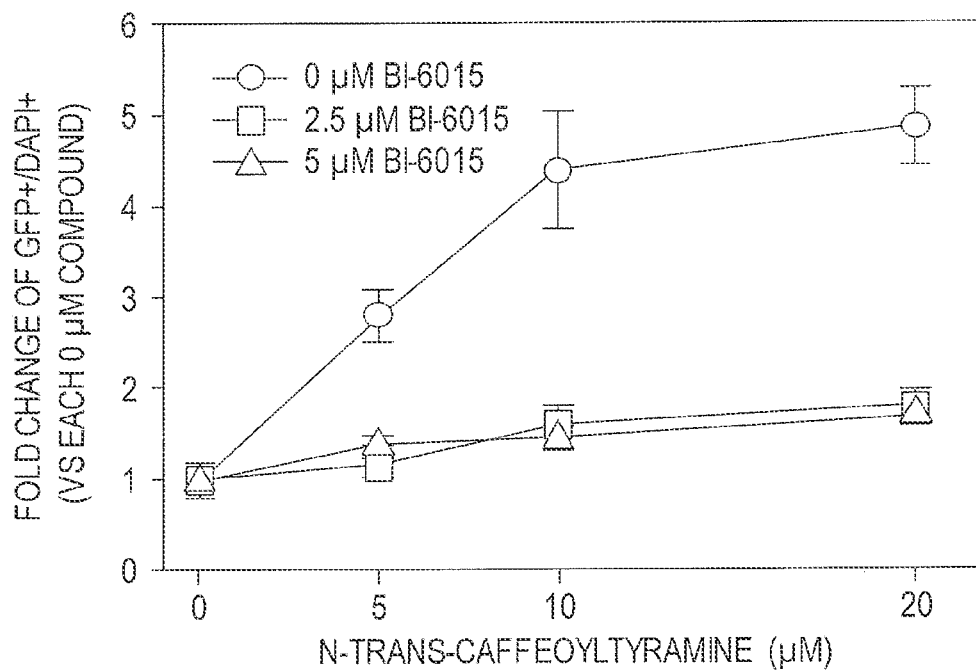
FIG. 4 shows that N-trans-caffeoyltyramine-mediated increases in insulin expression are inhibited by BI-6015, a known HNF4α antagonist.

Secondary experiments were performed to demonstrate that these compounds directly modulate HNF4α activity. In particular, it was demonstrated that insulin (FIG. 2) and HNF4α (FIG. 3) gene expression were upregulated (e.g., as determined by quantitative PCR analysis) in the presence of N-trans-caffeoyltyramine and N-trans-feruloyltyramine. In addition, it was found that p-coumaroyltyramine also upregulated insulin and HNF4a gene expression; however, cis-feruloyltyramine, N-coumaroyldopamine, N-transferuloyloctopamine and p-coumaroyloctopamine were inactive. Further, using the insulin promoter assay, N-trans-caffeoyltyramine-mediated increases in insulin expression were inhibited by BI-6015, a known HNF4α antagonist (FIG. 4).

Figure 5:
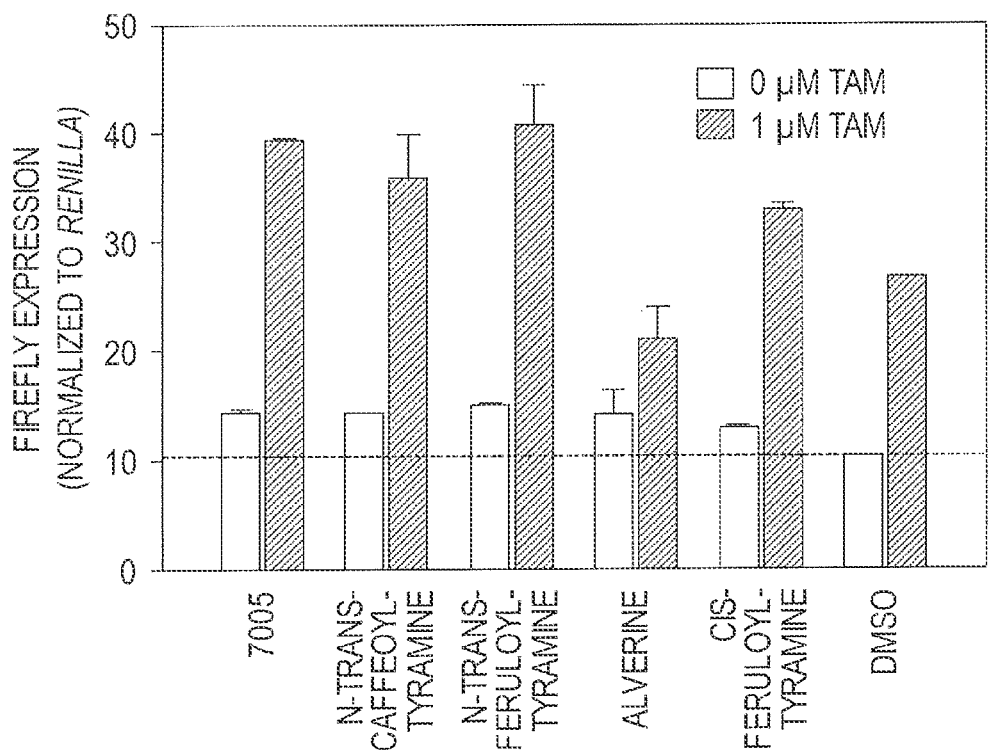
FIG. 5 shows the effect of N-trans-caffeoyltyramine and N-trans-feruloyltyramine on estrogenic activity. Assays were carried out in the presence (1 μM) or absence (0 μM) Tamoxifen (Tam) using Alverine and 7005 (CAS No. 380336-90-3) (known HNF4α transcriptional activators) as positive controls and cis-feruloyltyramine and DMSO as negative controls.

In addition, it was shown that N-trans-caffeoyltyramine and N-trans-feruloyltyramine did not exhibit estrogenic activity (FIG. 5).

Using human, rat and mouse hepatic microsomes, in vitro pharmacology indicated that N-trans-caffeoyl tyramine was stable and that higher bioactivity in humans may be attributed to the longer half-life of N-trans-caffeoyltyramine in human cells compared to mouse hepatic microsomes (Table 3). For human microsomes, the apparent major biotransformation pathway was oxidation of the left-hand aryl ring.

TABLE 3

| Microsomes | Amount* | Half-life (minutes) | Clearance Rate (µl/min/mg) | % Remaining |
|---|---|---|---|---|
| Mouse | 1 µM | 0.8 | 1762.2 | 0.4 |
|  | 10 µM | 6.9 | 200.4 | 0.3 |
| Rat | 1 µM | 2.1 | 674.2 | 0.6 |
|  | 10 µM | 22.4 | 30.9 | 33.6 |
| Human | 1 µM | 77.3 | 17.9 | 55.3 |
|  | 10 µM | 262.3 | 5.3 | 85.4 |

*Amount of N-trans-caffeoyltyramine

Figure 6:
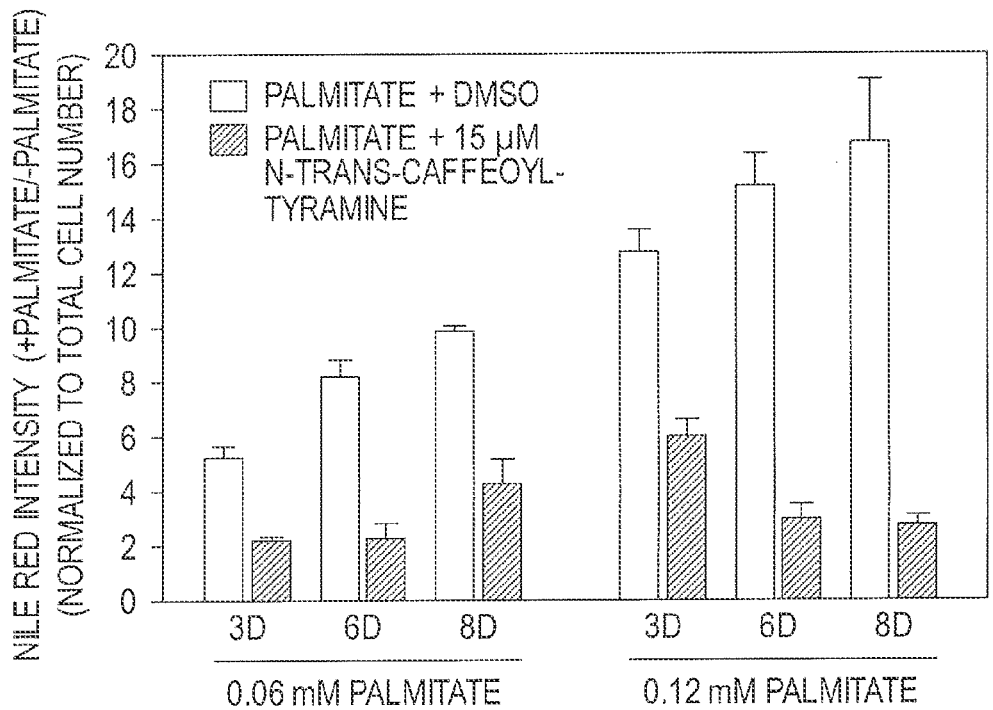
FIG. 6 demonstrates that N-trans-caffeoyltyramine and N-trans-feruloyltyramine can reverse fat accumulation. T6PNE cells were pretreated for 1 day with 0.06 mM, 0.12 mM or 0.25 mM palmitate at which time 15 μM N-trans-caffeoyltyramine or control (DMSO) was added. Cells were harvested on day 3, 6 and 8 and subjected to staining with Nile Red and Oil Red O. Results are expressed as fold change in Nile Red staining: +palmitate/10% FBS medium (no palmitate)

Analysis of HepG2 liver cells treated with N-trans-caffeoyltyramine (20 µM) or N-trans-feruloyltyramine (20 µM) indicated that these compounds were capable of clearing harmful fats from the liver, as evidenced by Oil Red O staining for fats, and further inhibited accumulation of fats in HepG2 liver cells treated with 0.25 mM palmitate. A similar inhibition of fat accumulation was observed in T6PNE cells treated with 0.25 mM palmitate and 10 µM N-trans-caffeoyltyramine, 10 µM N-trans-feruloyltyramine or 10 µM p-coumaroyltyramine. N-trans-caffeoyltyramine reduced lipid accumulation when palmitate was added prior to compound administration (FIG. 6).

In addition to performing assays demonstrating beneficial effects of the compounds of the present invention, initial safety/toxicity assays were performed. The collective results of these analyses are presented in Table 4.

TABLE 4

| Assay | N-trans-caffeoyl tyramine | N-trans-feruloyl tyramine | p-coumaroyl tyramine |
|---|---|---|---|
| HNF4α Activity | + | + | + |
| HNF4α mRNA | + | + | + |
| Insulin mRNA | + | + | + |
| Estrogenic Counter-Screen | + | + | + |
| Fat Clearance | + | + | ND |
| pH Stability | Acid Stable | Stable | Acid Stable |
| Bioavailability | ~11% | ~7% | ND |

ND, not determined

Example 3: Efficacy in Diet-Induced Obese Mice

In addition to demonstrating in vitro efficacy of the compounds of the present invention, experiments were performed in vivo in animal models of human disease, i.e., diet-induced obese mice. The experiments were performed to establish feeding and treatment regimen, dosing and administration regimens, as well as to provide evidence of beneficial effects of N-trans-caffeoyltyramine on glucose and lipid homeostasis, hepatic steatosis, β-cell function and hepatocyte function. Twelve mice (10 weeks old) were fed a high-fat diet for four weeks to induce obesity. After four weeks, and while on the high-fat diet, six mice were administered 5% DMSO or 120 mg/kg N-trans-caffeoyltyramine twice a day intraperitoneally for 14 days. One hour after the last i.p. injection of DMSO or N-trans-caffeoyl tyramine, the animals were sacrificed and blood and organ (liver, kidney, gut and pancreas) samples were collected. Organ samples were subjected to histological, RNA, triglyceride and protein analyses. Notably, the mice in this study did not exhibit any toxic effects at any of the doses tested. The mice receiving treatment displayed levels of activity, alertness, grooming, and appetite consistent with the control group. None of the treated mice exhibited weight loss, sickness, or abnormal behaviors compared to the control group.

Figure 7:
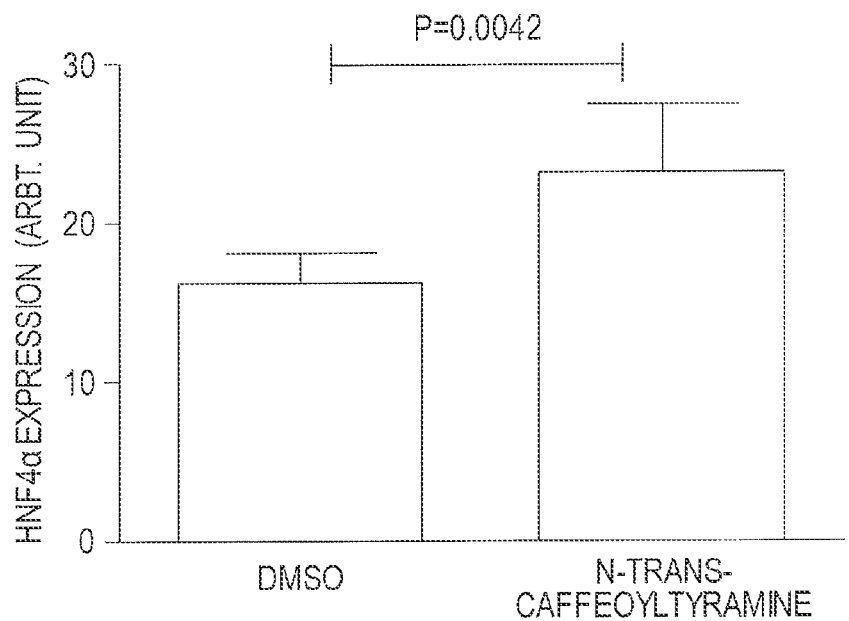
FIG. 7 shows that N-trans-caffeoyltyramine increases nuclear expression of HNF4α in the liver.
Figure 8:
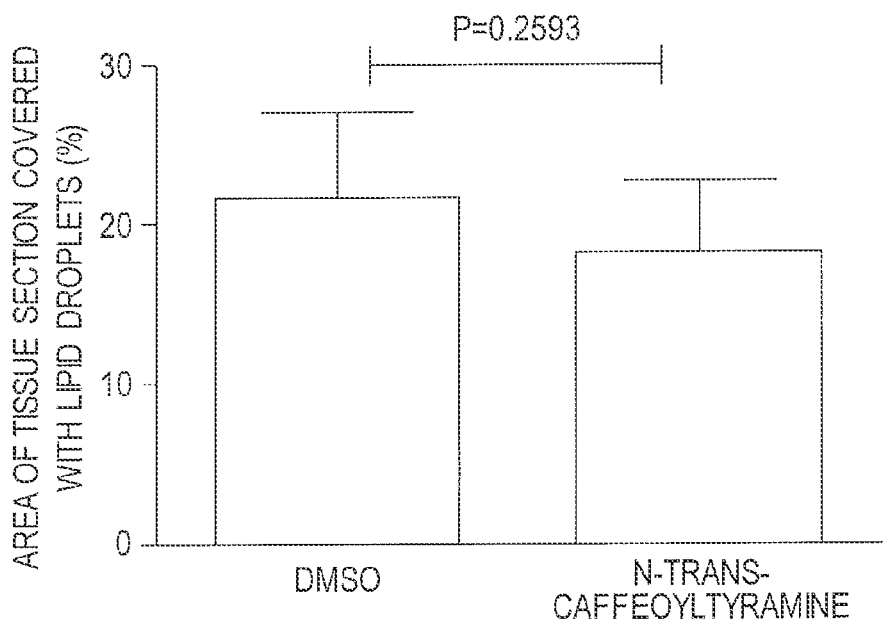
FIG. 8 shows that lipid droplet size in the liver is reduced by treatment with N-trans-caffeoyltyramine.
Figure 9:
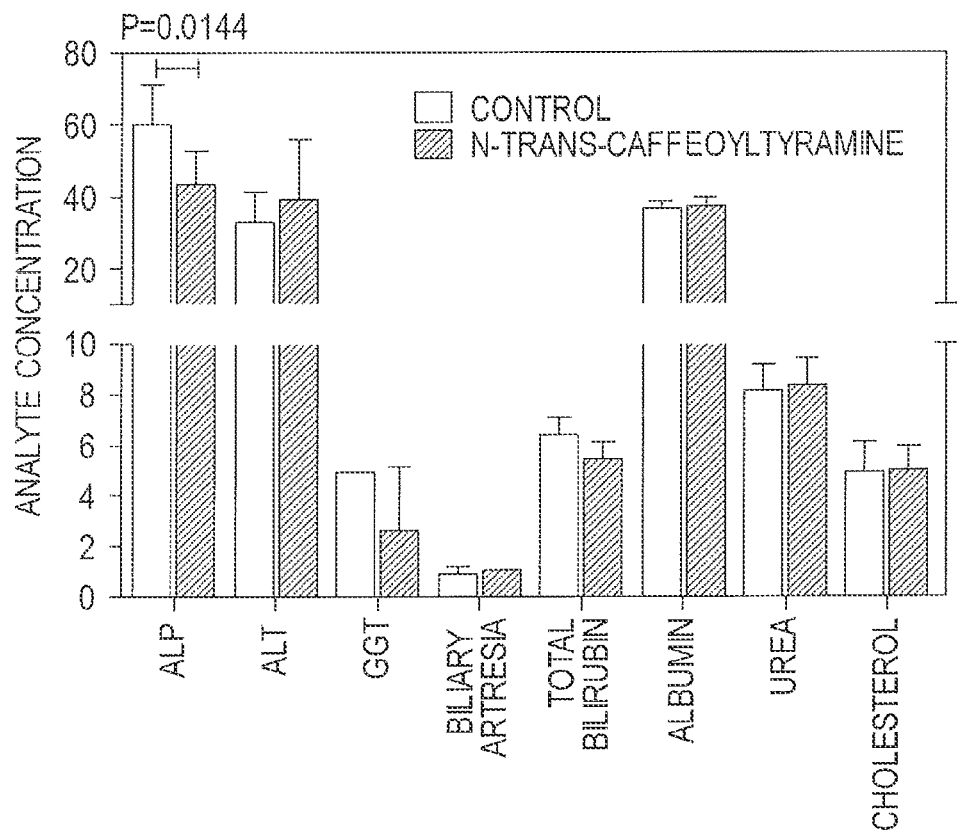
FIG. 9 shows levels of blood analytes alkaline phosphatase (ALP), alanine transaminase including (ALT), γ-glutamyltransferase (GGT), bilirubin, artresia, total albumin, albumin, blood urea nitrogen (urea), and cholesterol in mice treated with N-trans-caffeoyltyramine or control (DMSO).
Figure 10:
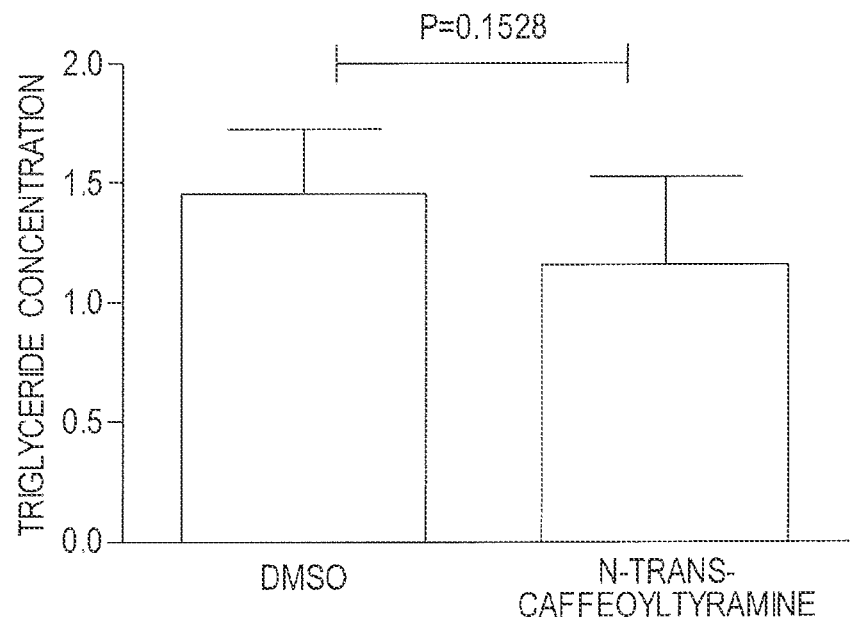
FIG. 10 shows triglyceride levels in the liver of mice fed a high fat diet and treated with N-trans-caffeoyltyramine or control (DMSO).
Figure 11:
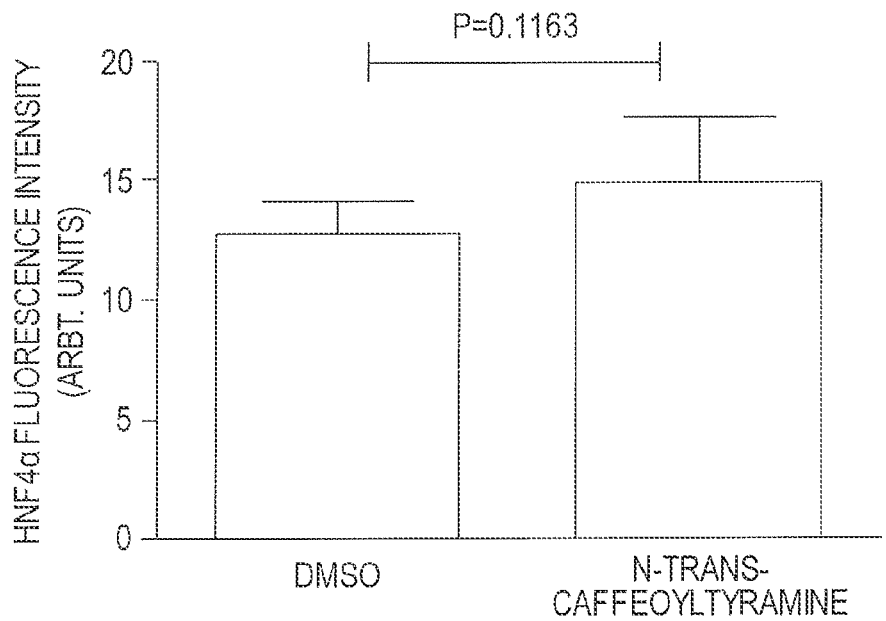
FIG. 11 shows the effect of N-trans-caffeoyltyramine on HNF4α expression in the pancreas of mice fed a high fat diet as compared to control (DMSO).
Figure 12:
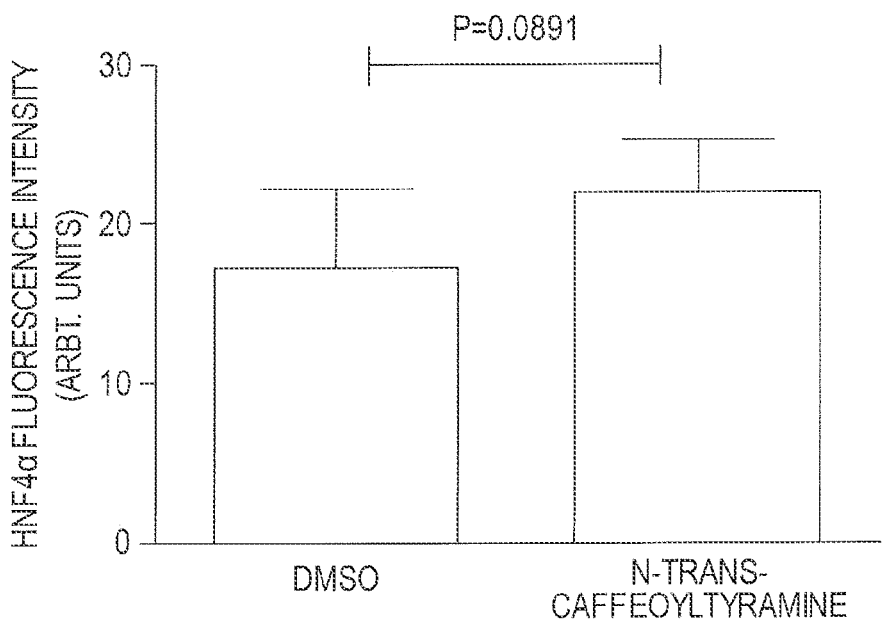
FIG. 12 shows the effect of N-trans-caffeoyltyramine on HNF4α expression in the intestine of mice fed a high fat diet as compared to control (DMSO).

Results showed that N-trans-caffeoyltyramine treatment decreased lipid accumulation and significantly increased HNF4α expression (P=0.0042) in the liver, in particular nuclear expression of HNF4α (FIG. 7). Immunostaining results indicated that N-trans-caffeoyltyramine increased HNF4α activity. In addition, lipid droplet sizes in the liver were reduced in N-trans-caffeoyltyramine-treated animals levels of alkaline phosphatase (FIG. 8 In addition, levels of alkaline phosphatase (FIG. 9) and triglycerides (FIG. 10) were significantly reduced in mice treated with N-trans-caffeoyltyramine. The reduction in liver fat and droplet size, and decrease in alkaline phosphatase demonstrate the beneficial effects of increasing HNF4α activity. Given that alkaline phosphatase and triglyceride levels are often a routine part of blood testing in humans, with elevated levels being an indication of poor liver functioning, obesity and metabolic syndrome, alkaline phosphatase and triglyceride levels would provide useful markers for assessing the effects of the tyramine containing hydroxycinnamic acid amides in humans administered compounds of the present invention. In the pancreas, HNF4α expression was increased in N-trans-caffeoyltyramine-treated animals, as compared to DMSO control mice (FIG. 11). Similarly, HNF4α expression was increased in intestines upon administration of N-trans-caffeoyltyramine (FIG. 12)

These in vivo data demonstrated a correlation between HNF4α expression and liver fat levels. In addition, results showed that N-trans-caffeoyltyramine increased HNF4α activity in vivo and produced beneficial effects on lipid, triglyceride, alkaline phosphatase and HNF4α levels.

Example 4: Evaluation of Compound-Related Toxicity

Given the need to balance benefits and risks of the compounds of the present invention, in vivo toxicity studies in laboratory animals (e.g., mice, rats, dogs) are typically performed. Such studies are typically performed consistent with *Good Laboratory Practice* (GLP) regulations to ensure reliability and reproducibility for regulatory purposes. If compounds are to be administered for periods of weeks to months to years in humans, chronic toxicity studies typically are performed (studies of from six months to one year in duration). For compounds to be used in foods, oral toxicity studies are recommended.

The purpose of chronic toxicity testing is to determine the toxicological profile of a test compound. In the initial phase of testing, a study will be performed in rats. A total of 160 Sprague Dawley rats (80 males and 80 females) approximately 5-7 weeks old and weighing between 80-100 g each will be randomly selected and allocated to treatment groups by weight; such that the mean body weights of each group will not be significantly different. The test compound or extract will be administered orally at dose levels of 0.5, 1 and 2 g/kg body weight per day to rats for a period of 180 consecutive days. The animals will be observed daily for any clinical signs of toxicity (e.g. r behavioral changes; skin and fur appearance; eating and drinking; etc.). At the end of the experiment, the animals will be subjected to hematological, biochemical and histopathological evaluation consistent with standard toxicological methods.

Example 5: Isolation of Tyramine Containing Hydroxycinnamic Acid Amides from Plant Sources Ethanolic extracts were prepared from various plant species and plant tissues thereof. Individual compounds were identified in the extracts by extracting dry plant powder material with 95% aqueous ethanol. The ethanol extract was concentrated and adsorbed onto celite and dry-loaded onto a C18 solid phase extraction column. The extract was desalted by washing with two column volumes of water which were collected and discarded. Compounds were eluted with two column volumes of methanol and the extract was concentrated to dryness. The extract was resuspended in 1:1 Acetonitrile:water prior to analysis. Synthetic standards of known concentrations were used to generate calibration curves prior to analysis. The listing of sources used in the analysis are presented below in Table 5. Plants are displayed for each compound in descending order with the plants that produce the highest amount of compound on the top of the list and the lowest producers at the bottom of the list.

TABLE 5

| Genus species | Plant Tissues (s) |
|---|---|
| N-Trans-caffeoyltryamine | |
| Annona muricate | Seed, pulp, skin |
| Annon spp. | Seed, pulp, skin |
| Tribulus terrestris | Seed, fruit |
| Cannabis sp. | Seed, hull, leaf |
| Annona cherimola | Seed, pulp, skin, leaf, wood |
| Annona montana | Leaf |
| Solanum lycoperscium | Fruit |
| Solanum tuberosum | Tuber, peel |
| Lycium barbarum | Fruit, stem |
| N-Trans-feruloyltyramine | |
| Annona sp. | Seed, pulp, skin |
| Annona cherimola | Seed, pulp, skin, leaf, wood |
| Piper nigrum | Fruit |
| Tribulus terrestris | Seed, fruit |
| Annona muricate | Seed, pulp, skin |
| Solanum lycopersicum | Fruit |
| Cannabis | Seed, hull, leaf |
| Capsicum frutescens | Fruit |
| Allium fistulosum | Aerial plant |
| Solanum tuberosum | Tuber, peel |
| Zea mays | Seed, stalk, leaf |
| Allium sativum | Bulb |
| Annona montana | Leaf |
| Annona squamosa | Fruit |
| Lycium barbarum | Fruit, stem |
| Capsicum annuum | Fruit |
| Ipomoea batatas | Peel |
| Chenopodium quinoa | Seed |
| Armoracia rusticana | Root |
| Capsicum annuum | Fruit, leaf, stem |
| Fagopyrum esculentum | Hull |
| Eragrostis tef | Seed |
| p-Courmaroyltyramine | |
| Annona spp. | Seed, pulp, skin |
| Tribulus terrestris | Seed, fruit |
| Solanum lycopersicum | Fruit |
| Annona muricate | Seed, pulp, skin |
| Annona montana | Leaf |
| Annona cherimola | Seed, pulp, skin, leaf, wood |

TABLE 5-continued

| Genus species | Plant Tissues (s) |
|---|---|
| Cannabis spp. | Seed, hull, leaf |
| Solanum tuberosum | Tuber, peel |
| Allium fistulosm | Aerial plant |
| Zea mays | Seed, stalk leaf |
| Allium sativum | Bulb |
| Ipomoea batatas | Peel |

Figure 13:
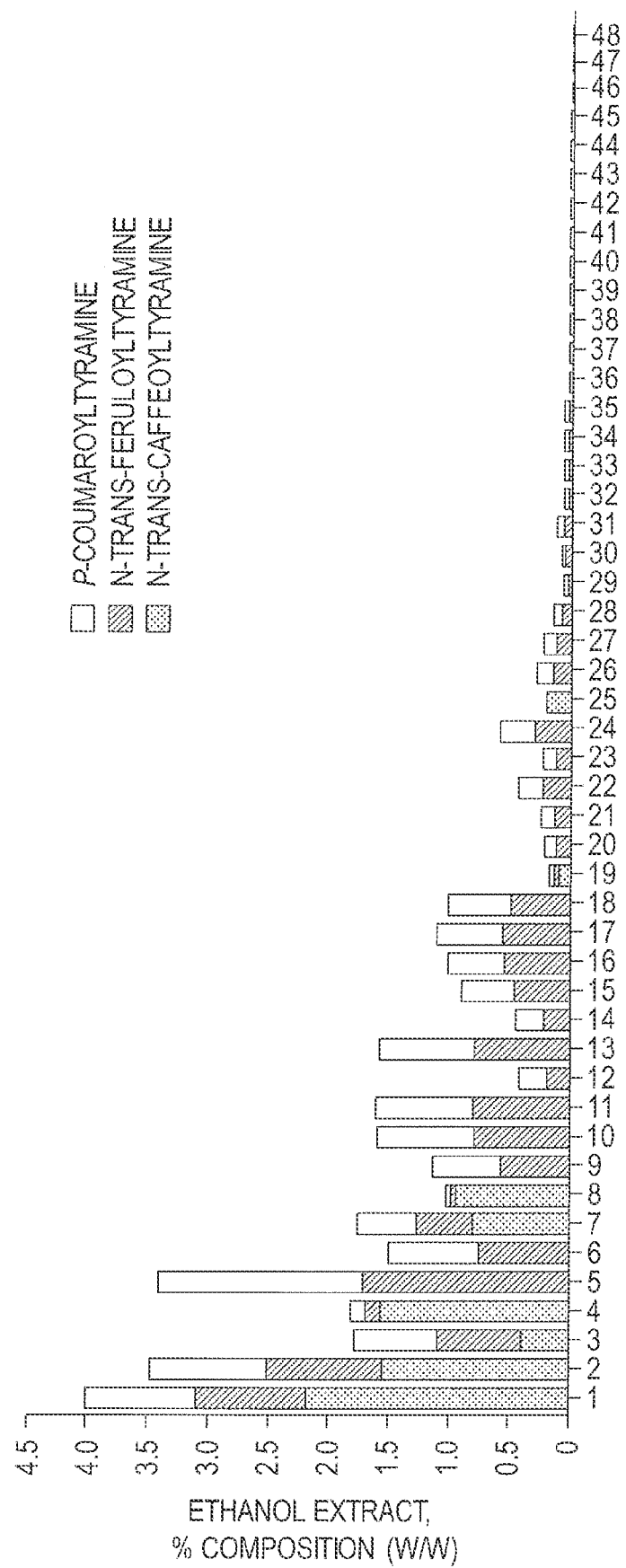
FIG. 13 shows the amounts of N-trans-caffeoyltyramine, N-trans-feruloyltyramine and p-coumaroyl tyramine present in ethanol extracts (% of extract, w/w) from a variety of sources including *Tribulus terrestris* seed (1), *Cannabis* (hemp) seed hull (2), *Annona* spp. (atemoya) seed (3), *Annona muricata* (Guanabana) seed (4), *A. cherimola* (Cherimoya) leaf (5), *Zea mays* stalk (6), *Tribulus terrestris* (Goat Head) seed (7), *A. cherimola* hardwood (bark and core) (8), *Solanum lycopersicum* ground pomace (9), *S. tuberosum* (yellow potato) peel (10), *Piper nigrum* (black peppercorn) fruit (11), *S. tuberosum* (purple potato) peel (12), *S. tuberosum* (red potato) peel (13), *S. lycopersicum* pomace (14), *S. lycopersicum* extruded pomace (15), *A. muricata* (Guanabana) leaves (16), *Allium sativum* (garlic) bulb (17), *S. tuberosum* (purple potato) peel (18), *A. montana* (Mountain soursop) leaves (19), *Z. mays* leaves (20), *S. tuberosum* (purple potato) sprouts (21), *A. cherimola* (Cherimoya) seed (22), *Allium fistulosum* (green onion) whole plant (23), *S. tuberosum* (white potato) peel (24), *A. cherimola* (Cherimoya) greenwood (25), *Cannabis* (hemp) leaves (26), *S. tuberosum* (white potato) peel (27), *S. lycopersicum* seed (28), *S. lycopersicum* (Beefsteak) whole fruit (29), *A. muricata* (Guarabana) skin of unripe fruit (30), *A. muricata* (Guanabana) ripe fresh fruit (31), *A. squamosa* (sweetsop) whole fruit (32), *Capsicum annuum* (serrano pepper) fruit (33), *S. tuberosum* (Russet potato) peel (34), *Lycium barbarum* (goji/wolf berry) fruit (35), *S. tuberosum* (purple potato) core (36), *Chenopodium quinoa* (quinoa) seed (37), *Ipomoea batatas* (sweet potato) whole potato (38), *Ipomoea batatas* (sweet potato) peel (39), *Armoracia rusticana* (horseradish) root (40), *S. tuberosum* (Colorado potato) peel (41), *Fagopyrum esculentum* (buckwheat) hulls (42), *Capsicum frutescens* (piri piri pepper) fruit (43), *S. tuberosum* (purple potato) core (44), *C. annuum* (Thai chili) stems and leaves (45), *A. muricata* (Guanabana) unripe fruit flesh (46), *S. tuberosum* (yellow potato) core (47), *and Eragrostis tef* (teff) seed (48).

The amounts of N-trans-caffeoyltyramine, N-transferuloyltyramine and p-coumaroyltyramine present in certain ethanol extracts (% of extract, w/w) was determined. Quantification of the compounds was performed by normalizing the results by the weight of the ethanol extracts. The results of these analyses are presented in FIG. 13.

Example 6: Efficacy of Test Compounds in an Animal Model of NAFLD

Like the diet-induced obese mouse model, there are other well-established animal models for examining the benefits of compounds in NAFLD.

Animals and Diets.

Adult male Sprague-Dawley rats (250-300 grams) will be obtained. Custom-prepared diets including control, High-fat only, and High-fat diet containing the test compound or extract. Control diet will be a low-fat diet where 12% of total calories are from corn oil, while most of the fat is linoleic acid. The High-fat (HF) diet will contain 60% of total calories as lard as well as 2% corn oil, and the diet will be enriched in oleic acid and the saturated fatty acids palmitic and stearic. Such a High-fat diet was previously used to induce NAFLD in rats (Carmiel-Haggai, et al. (2005) *FASEB J.* 19:136-138). Seven rats in each of the 4 groups will be randomized and fed the diets for 4 weeks: Group I: control diet; Group II: HF diet, Group III: HF+0.5% compound/extract diet; Group IV: HF+1% compound/extract. The rats will be placed on a 12-hour day/night cycle and provided ad libitum access to food and water. At the end of 4 weeks, rats will be fasted 16-18 hours, anesthetized, and blood and liver samples will be collected for biochemical and histological analyses.

Serum and Liver Triglyceride and Cholesterol.

Serum triglyceride and total cholesterol will be measured by commercially available assay kits (e.g., Wako Diagnostics; Richmond, Va.). Total lipid will be extracted from liver samples (about 0.25 g) with chloroform-methanol mixture (2:1) and washed with 0.73% sodium chloride solution. The organic and aqueous phases will be separated by centrifugation at 2000 rpm for 10 minutes. The organic phase containing total lipid will be dried completely under nitrogen and lipid extract reconstituted in isopropanol. An aliquot of lipid extract will be used to measure triglycerides and total cholesterol using assay kits (e.g., from Wako Diagnostics).

Measurement of Serum and Liver Thiobarbituric Acid-Reactive Substances (TEARS).

Serum and liver TEARS will be measured as an index of lipid peroxidation products.

Liver Histology.

Liver samples will be fixed in 10% formalin and embedded in paraffin. Sections (5 μm) will be stained with hematoxylin and eosin and evaluated by a pathologist who will be blinded from the experimental groups and conditions. Sections will be subjected to semi-quantitation for assessing steatosis.

Statistical Analysis.

Data will be presented as mean+S.E. Statistical analyses for the groups will be made using a two-tailed Student's t-test, and p<0.05 will be considered statistically significant.

Example 7: an Evaluation of the Safety and Efficacy of Test Compounds in Treating Nash in Subjects with T2DM The objective of the study will be to assess whether the example compound or extract can improve liver health and liver fat content, as compared with placebo, in subjects who suffer from T2DM and NASH. The study also will include assessment of serum alanine aminotransferase (ALT) levels, and determining whether test compound or extract treatment is more effective than placebo treatment in reducing liver fat content when measured by MRI-derived proton density-fat fraction (MRI-POFF). The comparison of serum ALT levels and liver fat content between compound or extract treatment and placebo treatment will be conducted in adult subjects with NASH and T2DM at week 24 (or the last postbaseline observation).

The secondary objectives of the study will be to evaluate the effects of the test compound or extract compared with placebo treatment on liver heath by assessing serum AST levels after 24 weeks of treatment; evaluate the effects of treatment on glycosylated hemoglobin (HbA1c); evaluate the effects of treatment on liver fibrosis, as measured using transient Elastography with Fibroscan. Considered together, the results will allow for assessment of overall safety and tolerability of test compound or extract treatment as compared with placebo treatment.

Additionally, several exploratory objectives will be included in the study design. For example, the effect of the test compound or extract on the immune profile of subjects based on 1) a change from baseline in high-sensitivity C-reactive protein (hsCRP) and erythrocyte sedimentation rate (ESR); 2) a change from baseline in serum levels of tumor necrosis factor alpha (TNF-$\alpha$); 3) a change from baseline in levels of transforming growth factor (TGF) beta; 4) a change from baseline in levels of interleukin (IL) -2, -4, -6, -10, and -12; and interferon (IFN) gamma; and 5) a fluorescence-activated cell sorting (FACS) analysis, which will measure a change from baseline in immunological markers such as cluster of differentiation 3 (CD 3), CD4, CD8, CD25, CD40, CD56, CD69, CD127, forkhead box P3 (FOXP3+), IL17, and retinoic acid-related orphan receptor-$\gamma$t (ROR$\gamma$t)). Yet another exploratory objective will be to evaluate the effects of the test compound or extract on blood inflammatory markers (TNF-$\alpha$, fibroblast growth factor 19 (FGF-19)), liver fibrosis or cell death markers (cytokeratin-18 (CK-18), soluble Fas (sFas)), and oxidative stress markers such as hydroxyeicosatetraenoic acids (HETEs), hydroxyoctadecadienoic acids (HODEs), oxoeicosatetraenoic acids (oxoETEs), oxooctadecadienoic acids (oxoODEs)) and ox-nonalcoholic steatohepatitis (ox-NASH). Moreover, the study will: evaluate the effect of the test compound or extract using the homeostatic model assessment of insulin resistance (HOMA IR) to measure insulin; evaluate the effect of the compound or extract on serum lipid profile (triglycerides, high-density lipoprotein (HDL), low-density lipoprotein (LDL), and total cholesterol); and evaluate the effect of the compound or extract on GLP1 and adiponectin.

Safety or tolerability endpoints will be evaluated after 24 weeks of treatment with the test compound or extract. Endpoints will include assessment of: the number and severity of any reported adverse events; physical examination findings, clinical laboratory evaluations (serum chemistry, hematology, and urinalysis) and 12-lead electrocardiograms (ECGs) from baseline to study completion; and the number of subjects that withdraw from the study before completion of the protocol. The safety laboratory test results will be collected and measured at the following time points during the study: days-1 and 3 and weeks 1, 2, 3, 4, 6, 8, 10, 12, 14, 16, 18, 20, 22, and 24 (or early withdrawal).

A total of 80 T2DM and NASH subjects will be randomized into two groups: one group will receive a placebo, once daily (n=40); and one group will receive a dose of the test compound or extract, 80 mg, once daily (n=40). Although test compound or extract will be administered at a dose of 80 mg per day, the dose may be titrated based on subject tolerability, or it may be set at a fixed amount for the duration of the study, regardless of tolerability.

Example 8: an Evaluation of the Safety and Efficacy of Test Compounds in Treating Nash in Obese Subjects A study will be conducted according to the methods of Example 7, wherein the only difference is that the subject inclusion criteria include the requirement that the subjects are obese, as defined as having a BMI of ≥30 instead of T2DM.

Example 9: an Evaluation of the Safety and Efficacy of Test Compounds in Treating NAFLD in Subjects with T2DM The purpose of this study will be to determine whether the test compound or extract can improve liver fat content and liver health, as compared with placebo, in subjects who suffer from both T2DM and NAFLD by assessing magnetic resonance imaging-derived proton density fat fraction (MRI-PDFF) after 24 weeks of treatment.

The secondary objectives of this study will be: 1) to evaluate the effects of test compound or extract treatment, as compared with placebo treatment, on liver health by assessing serum ALT levels after 24 weeks of treatment; 2) to evaluate the effects of test compound or extract treatment, as compared with placebo treatment, on liver heath by assessing serum AST levels after 24 weeks of treatment; 3) to evaluate the effects of test compound or extract treatment on glycosylated hemoglobin (HbA1c); 4) to evaluate the effects of test compound or extract treatment on liver fibrosis, as measured using transient Elastography with Fibroscan; and 5) to evaluate the overall safety and tolerability of test compound or extract treatment as compared with placebo treatment. Exploratory objectives of this study include those listed in Example 7.

A total of 80 T2DM and NAFLD subjects will be randomized into two groups: one group will receive a placebo, once daily (n=40) and one group will receive a dose of test compound or extract, 80 mg, once daily (n=40) as described in Example 7. Subjects will be screened at visit 1 between days −28 and −2. At screening, subjects will undergo screening procedures meant to ensure that inclusion/exclusion criteria are met, including an abdominal MRI to quantitatively measure liver fat content. Subjects who meet inclusion/exclusion criteria based on the results of screening assessments will return to the study center on day −1 to undergo baseline assessments (visit 2). At the baseline visit, confirmation of inclusion/exclusion criteria will be performed, and assessments of baseline laboratory values, physical examination findings, and ECG results also will be performed.

Subjects will be required to have a certified histology report which documents and assesses the degree of steatosis, lobular inflammation, hepatocyte ballooning, and fibrosis that confirms a diagnosis of NAFLD.

At visit 18 on week 24 (or at early termination), all subjects will undergo end of treatment assessments, including liver fat content imaging by MRI and clinical laboratory safety assessments.

What is claimed is:

1. An oral composition comprising:
a compound for oral consumption having the structure of Formula I, or an isomer, salt, homodimer, heterodimer or conjugate thereof:

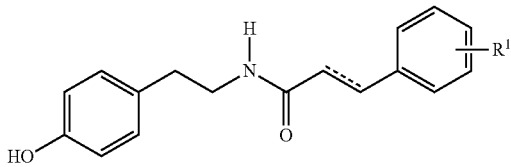

Formula I wherein
$R^1$ is present or absent, and when present is a substituent on one or more ring atoms and is for each ring atom independently a hydroxy group, halo group, substituted or unsubstituted lower alkyl group, or substituted or unsubstituted lower alkoxy group;
the dashed bond is present or absent;
N-trans-feruloyltyramine, or a salt thereof; and
a carrier,
wherein the compound for consumption having the structure of Formula I is N-trans-caffeoyltyramine and comprises between 0.1% to 99% of the composition,
wherein the oral composition is a powder.

2. The composition of claim 1, further comprising p-coumaroyltyramine.

3. The composition of claim 1, wherein the carrier is selected from at least one of a sugar, a starch, cellulose, powdered tragacanth, malt, gelatin, talc, excipient, oil, glycol, polyol, ester, agar, buffering agent, alginic acid, isotonic saline, ethyl alcohol, pH buffered solutions, or polyesters.

4. The composition of claim 1, wherein the composition is formulated in a tablet or capsule.

5. A dietary supplement, food ingredient or additive, a medical food, nutraceutical, or pharmaceutical comprising a compound for oral consumption having the structure of Formula I, or an isomer, salt, homodimer, heterodimer or conjugate thereof:

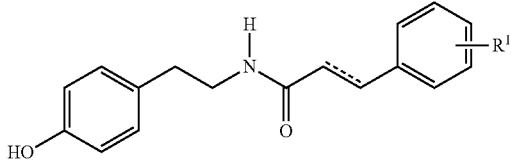

Formula I wherein
$R^1$ is present or absent, and when present is a substituent on one or more ring atoms and is for each ring atom independently a hydroxy group, halo group, substituted or unsubstituted lower alkyl group, or substituted or unsubstituted lower alkoxy group;
the dashed bond is present or absent;
N-trans-feruloyltyramine, or a salt thereof;
a carrier; and
a preservative,
wherein the compound for oral consumption having the structure of Formula I is N-trans-caffeoyltyramine and comprises between 0.1% to 99% of the dietary supplement, food ingredient or additive, medical food, nutraceutical, or pharmaceutical,
wherein the dietary supplement, food ingredient or additive, a medical food, or nutraceutical is a powder.

6. The dietary supplement, food ingredient or additive, a medical food, nutraceutical, or pharmaceutical of claim 5, wherein the preservative is from about 0.01% to 1% by weight of the dietary supplement, food ingredient or additive, medical food, nutraceutical, or pharmaceutical.

7. The dietary supplement, food ingredient or additive, a medical food, nutraceutical, or pharmaceutical of claim 5, wherein the preservative is selected from at least one of sodium benzoate, methyl paraben, propyl paraben, sodium nitrite, sulphur dioxide, sodium sorbate, potassium sorbate or salts of edetate.

8. The oral composition of claim 1, further comprising cinnamoyltyramine, sinapoyltyramine, 5-hydroyferultyramine, or a combination thereof.

9. The oral composition of claim 1, wherein the oral composition has a pH between 2 and 7.4.

10. The oral composition of claim 3, wherein the cellulose is carboxymethylcellulose.

11. The oral composition of claim 1, wherein the N-trans-caffeoyltyramine comprises between 10% to 99% of the composition.

12. The oral composition of claim 1, wherein the composition comprises about 10 mg to about 60 mg of N-trans-caffeoyltyramine and N-trans-feruloyltyramine.

13. The oral composition of claim 1, wherein the N-trans-caffeoyltyramine and the N-trans-feruloyltyramine are an extract of *Cannabis* (hemp) seed hull.

14. The dietary supplement of claim 5, further comprising cinnamoyltyramine, sinapoyltyramine, 5-hydroyferultyramine, or a combination thereof.

15. The dietary supplement of claim 5, wherein the pH of the dietary supplement, food ingredient or additive, a medical food, or nutraceutical is between 2 and 7.4 has a pH between 2 and 7.4.

16. The dietary supplement of claim 5, wherein the carrier is selected from the group consisting of cellulose, wax, and ester.

17. The dietary supplement of claim 16, wherein the cellulose is carboxymethylcellulose.

18. The dietary supplement of claim 5, wherein the N-trans-caffeoyltyramine comprises between 10% to 99% of the dietary supplement, food ingredient or additive, a medical food, nutraceutical, or pharmaceutical.

19. An oral composition comprising:
a compound for oral consumption having the structure of Formula I, or an isomer, salt, homodimer, heterodimer or conjugate thereof:

Formula I

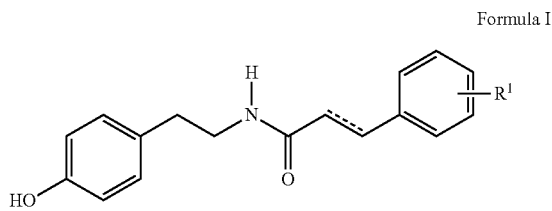

wherein
R¹ is present or absent, and when present is a substituent on one or more ring atoms and is for each ring atom independently a hydroxy group, halo group, substituted or unsubstituted lower alkyl group, or substituted or unsubstituted lower alkoxy group;
the dashed bond is present or absent;
p-coumaroyltyramine, or a salt thereof; and
a carrier,
wherein the compound for oral consumption having the structure of Formula I is N-trans-caffeoyltyramine and comprises between 0.1% to 99% of the composition,
wherein the composition is a powder.

20. The composition of claim 19, wherein the carrier is selected from at least one of a sugar, a starch, cellulose, powdered tragacanth, malt, gelatin, talc, excipient, oil, glycol, polyol, ester, agar, buffering agent, alginic acid, isotonic saline, ethyl alcohol, pH buffered solutions, or polyesters.

21. The composition of claim 19, further comprising cinnamoyltyramine, sinapoyltyramine, 5-hydroyferultyramine, or a combination thereof.

22. The composition of claim 19, wherein the composition is formulated in a tablet or capsule.

23. The oral composition of claim 20, wherein the cellulose is carboxymethylcellulose.

24. The oral composition of claim 19, wherein N-trans-caffeoyltyramine comprises between 10% to 99% of the composition.

25. A dietary supplement, food ingredient or additive, a medical food, nutraceutical, or pharmaceutical comprising a compound for oral consumption having the structure of Formula I, or an isomer, salt, homodimer, heterodimer or conjugate thereof:

Formula I

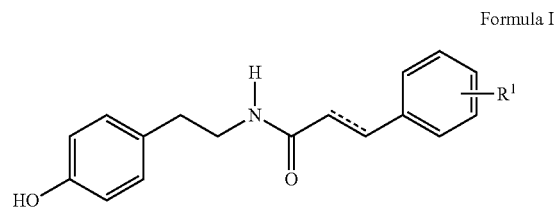

wherein
R¹ is present or absent, and when present is a substituent on one or more ring atoms and is for each ring atom independently a hydroxy group, halo group, substituted or unsubstituted lower alkyl group, or substituted or unsubstituted lower alkoxy group;
the dashed bond is present or absent; and
p-coumaroyltyramine, or a salt thereof;
a carrier; and
a preservative,
wherein the compound for oral consumption having the structure of Formula I is N-trans-caffeoyltyramine and comprises between 0.1% to 99% of the dietary supplement, food ingredient or additive, a medical food, nutraceutical, or pharmaceutical,
wherein the dietary supplement, food ingredient or additive, a medical food, or nutraceutical is a powder.

26. The dietary supplement, food ingredient or additive, a medical food, nutraceutical, or pharmaceutical of claim 25, wherein the preservative is from about 0.01% to 1% by weight of the dietary supplement, food ingredient or additive, a medical food, nutraceutical, or pharmaceutical.

27. The dietary supplement, food ingredient or additive, a medical food, nutraceutical, or pharmaceutical of claim 25, wherein the N-trans-caffeoyltyramine comprises between 10% to 99% of the dietary supplement, food ingredient or additive, a medical food, nutraceutical, or pharmaceutical.

28. The dietary supplement of claim 25, further comprising cinnamoyltyramine, sinapoyltyramine, 5-hydroyferultyramine, or a combination thereof.

29. The dietary supplement of claim 25, wherein the carrier is selected from the group consisting of cellulose, waxes, oils and esters.

30. The oral composition of claim 29, wherein the cellulose is carboxymethylcellulose.

* * * * *